(12) United States Patent
Doughty et al.

(10) Patent No.: US 10,424,402 B1
(45) Date of Patent: Sep. 24, 2019

(54) SYSTEM AND METHOD FOR GEOGRAPHIC MAPPING OF BASE DATA

(75) Inventors: Pamela D. Doughty, Frisco, TX (US);
Dwight E. Carter, Denton, TX (US);
Michelle Erickson, Gastonia, NC (US);
Nicole Johnson, Dallas, TX (US);
Janet Burkhard, Dallas, TX (US)

(73) Assignee: Dallas-Fort Worth Hospital Council Education and Research Foundation, Irving, TX (US)

( * ) Notice: Subject to any disclaimer, the term of this patent is extended or adjusted under 35 U.S.C. 154(b) by 211 days.

(21) Appl. No.: 13/303,104

(22) Filed: Nov. 22, 2011
(Under 37 CFR 1.47)

Related U.S. Application Data

(60) Provisional application No. 61/416,149, filed on Nov. 22, 2010.

(51) Int. Cl.
*G06F 19/00* (2018.01)
*G06Q 50/22* (2018.01)
*G16H 10/60* (2018.01)

(52) U.S. Cl.
CPC .................. *G16H 10/60* (2018.01)

(58) Field of Classification Search
CPC ............. G06F 19/3443; G06F 19/3493; G06F 19/322; G06F 17/30265; G06Q 50/22; G16H 10/00; G16H 80/00
USPC .......................................................... 705/3
See application file for complete search history.

(56) References Cited

U.S. PATENT DOCUMENTS

| | | | |
|---|---|---|---|
| 2003/0177132 A1 | 9/2003 | Thomas et al. | |
| 2004/0078228 A1 | 4/2004 | Fitzgerald et al. | |
| 2004/0148195 A1* | 7/2004 | Kalies | G06F 19/322 705/2 |
| 2005/0158767 A1 | 7/2005 | Haskell et al. | |
| 2007/0106754 A1* | 5/2007 | Moore | 709/217 |
| 2007/0219964 A1* | 9/2007 | Cannon | G06F 17/30265 |
| 2009/0061902 A1* | 3/2009 | Abhyanker | H04L 12/18 455/456.3 |
| 2009/0082997 A1* | 3/2009 | Tokman et al. | 702/179 |
| 2011/0161096 A1 | 6/2011 | Buehler et al. | |

OTHER PUBLICATIONS

DFWHC Education and Research Foundation, "REMPI Regional Enterprise Master Patient Index", Jun. 30, 2009, 1 page.
(Continued)

*Primary Examiner* — Hiep V Nguyen
(74) *Attorney, Agent, or Firm* — Winstead PC

(57) ABSTRACT

A method includes receiving, by a server computer, a selection of patient records. The method further includes aggregating the patient records by geographic unit based on at least one healthcare metric. In addition, the method includes accessing a map of a geographic region covered by the selected patient records. Further, the method includes annotating the map based on a geographic variance of the at least one healthcare metric. The method also includes receiving, by the server computer, a selection of at least one environmental factor. Additionally, the method includes aggregating, by the server computer, environmental data for the environmental factor by the geographic unit. The method further includes annotating the map based on a geographic variance of the environmental factor.

18 Claims, 32 Drawing Sheets

(56) References Cited

OTHER PUBLICATIONS

DFWHC Education and Research Foundation, "One of the first of its kind—patient safety and quality care service launched in Dallas-Fort Worth Area", Jun. 30, 2009, 1 page.
Carter, Dwight, "What's Your Data Doing?", Mar. 19, 2009, 22 pages.
Dallas-Fort Worth Hospital Council Education & Research Foundation, "Regional Electronic Master Patient Index (REMPI) Record Linkage Project Improving Patient Safety, Quality & Health", Mar. 19, 2009, 9 pages.

* cited by examiner

SYSTEM AND METHOD FOR GEOGRAPHIC MAPPING OF BASE DATA

CROSS-REFERENCE TO RELATED APPLICATIONS

This application claims priority from, and incorporates by reference the entire disclosure of, U.S. Provisional Application No. 61/416,149 filed on Nov. 22, 2010.

BACKGROUND

Technical Field

The present invention relates generally to data management and more specifically, but not by way of limitation, to systems and methods for geographic mapping of data.

History of Related Art

Patients routinely have patient encounters with numerous healthcare providers including, but not limited to, clinics, hospitals, and other medical facilities. The patient encounter may be a doctor's visit, an inpatient hospital stay, or the like. Healthcare providers usually independently maintain patient-encounter data for current and former patients for purposes of medical recordkeeping. The patient-encounter data may be stored and maintained to facilitate, for example, future provision of services, billing or evaluative functions, or other functions.

As described above, at least some manner of healthcare data abounds nearly everywhere. However, traditionally, this data is of almost no use for purposes of determining, for example, causal or associative factors for a disease or condition. This is because such factors are often latent and cannot generally be identified just by looking at results-oriented data. Rather, extensive research is usually necessary. As a result, data about potential environmental factors that can affect, for example, a healthcare issue or disease, is difficult to garner and leverage for research in an efficient manner.

SUMMARY OF THE INVENTION

In one embodiment, a method includes receiving, by a server computer, a selection of patient records. The method further includes aggregating the patient records by geographic unit based on at least one healthcare metric. In addition, the method includes accessing a map of a geographic region covered by the selected patient records. Further, the method includes annotating the map based on a geographic variance of the at least one healthcare metric. The method also includes receiving, by the server computer, a selection of at least one environmental factor. Additionally, the method includes aggregating, by the server computer, environmental data for the environmental factor by the geographic unit. The method further includes annotating the map based on a geographic variance of the environmental factor.

In one embodiment, a computer-program product includes a computer-usable medium having computer-readable program code embodied therein, the computer-readable program code adapted to be executed to implement a method. The method includes receiving, by a server computer, a selection of patient records. The method further includes aggregating the patient records by geographic unit based on at least one healthcare metric. In addition, the method includes accessing a map of a geographic region covered by the selected patient records. Further, the method includes annotating the map based on a geographic variance of the at least one healthcare metric. The method also includes receiving, by the server computer, a selection of at least one environmental factor. Additionally, the method includes aggregating, by the server computer, environmental data for the environmental factor by the geographic unit. The method further includes annotating the map based on a geographic variance of the environmental factor.

BRIEF DESCRIPTION OF THE DRAWINGS

A more complete understanding of the method and apparatus of the present invention may be obtained by reference to the following Detailed Description when taken in conjunction with the accompanying Drawings wherein.

DETAILED DESCRIPTION OF ILLUSTRATIVE EMBODIMENTS OF THE INVENTION

During the course of conducting commerce or other transactions, databases are frequently developed that store information useful for a particular purpose. For example, data warehouses may be developed to store information related to retail outlets, sales, crime, healthcare, etc. For purposes of this patent application, already-existing stored information as described above is referred to herein as base data.

Base data as described above is frequently analyzed to generate useful analytics such as, for example, statistical data. In various embodiments, geographic information already stored as part of the base data can be leveraged to generate new layers of useful information beyond what is stored in the database. For example, the base data may already include geographic information such as, for example, ZIP codes, cities, metropolitan areas, states, countries, geographic coordinates, etc. In various embodiments, the geographic information can be supplemented with maps and environmental data that, in combination, help identify and analyze previously unknown geographic trends for the base data and help visualize both the base data and the geographic trends.

As used herein, environmental data is data about circumstances, objects, or conditions related to a geographic unit. Circumstances, objects, or conditions that environmental data describes may be referred to herein as environmental factors. Environmental data may concern various environmental factors such as, for example, physical characteristics (e.g., terrain), educational statistics, availability of various resources (e.g., grocery resources, healthcare, etc.), air quality, and many other categories of information. In general, environmental data is logically separate from base data that is maintained as part of the operation of a system.

Figure 16:
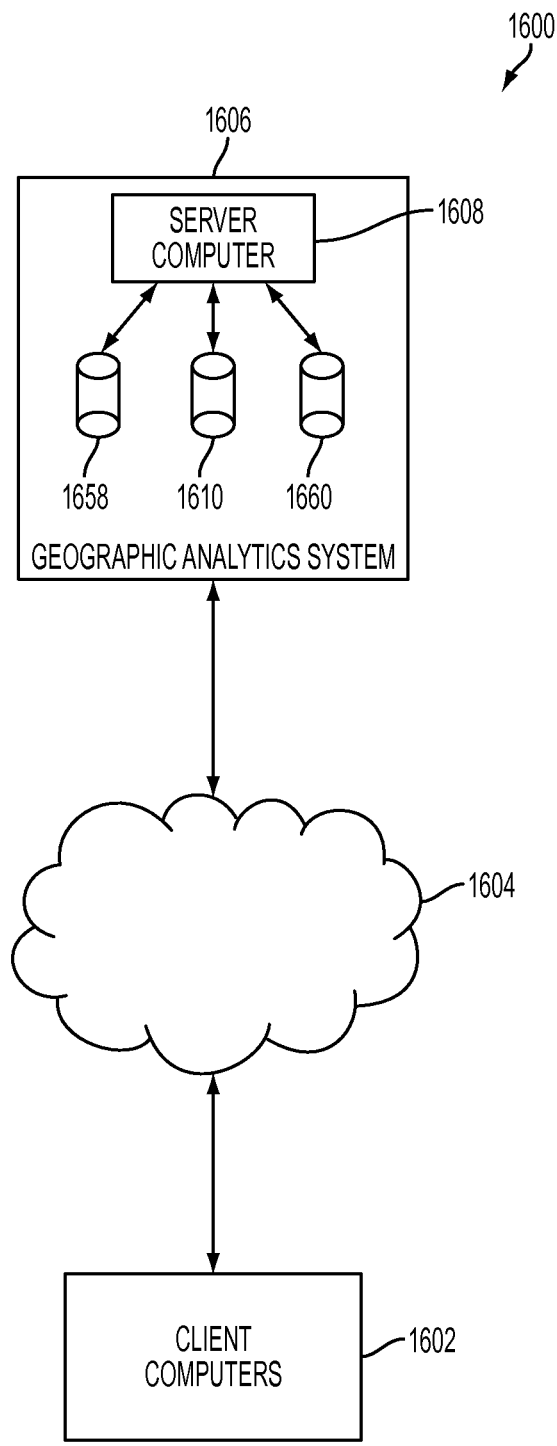
FIG. 16 illustrates a system for generating geographic analytics from base data.

FIG. 16 illustrates a system 1600 for generating geographic analytics from base data. The system 1600 includes a geographic analytics system 1606, a network 1604, and one or more client computers 1602. The network 1604 may be a computer network such as, for example, the Internet. The geographic analytics system 1606 includes at least one server computer 1608, a data warehouse 1610, a map repository 1658, and an environmental-data repository 1660.

The data warehouse 1610 typically stores base data that, for example, is collected during the ordinary course of operation. The data warehouse 1610 may include, for example, sales data, crime data, customer data, healthcare data, or any other kind of base data. The base data stored by the data warehouse 1610 includes at least some geographic information. For example, the data warehouse 1610 may store ZIP codes, cities, counties, states, countries, or the like for records stored therein. The map repository 1058 typically includes maps suited to cover geographic units for which the data warehouse 1610 stores data. The environmental-data repository 1660 includes a set of environmental data for each of a plurality of environmental factors. The environmental-data repository 1660 is typically indexed by at least one geographic unit such as, for example, ZIP code.

The at least one server computer 1608 has an analytics application operating thereon that is accessible to the one or more client computers 1602 via, for example, a web interface over the network 1604. The analytics application on the at least one server computer 1608 is operable to access the data warehouse 1610, the map repository 1058, and the environmental-data repository 1660 for purposes of developing geographic analytics. An exemplary process for generating geographic analytics will be described with respect to FIGS. 17 and 18.

One of ordinary skill in the art will appreciate that the at least one server computer 1608 is exemplary in nature and is shown in order to describe various inventive features to one of ordinary skill in the art. The geographic analytics system 1606 may utilize any number of physical or virtual server computers to perform any functionality described herein with respect to the at least one server computer 1608 or the geographic analytics system 1606. The data warehouse 1610, the maps repository 1658, and the environmental-data repository 1660 are similarly exemplary in nature. After reviewing the inventive principles described herein, one of ordinary skill in the art will appreciate that a given implementation of the geographic analytics system 1606 may utilize more or fewer databases to achieve similar functionality.

Figure 17:
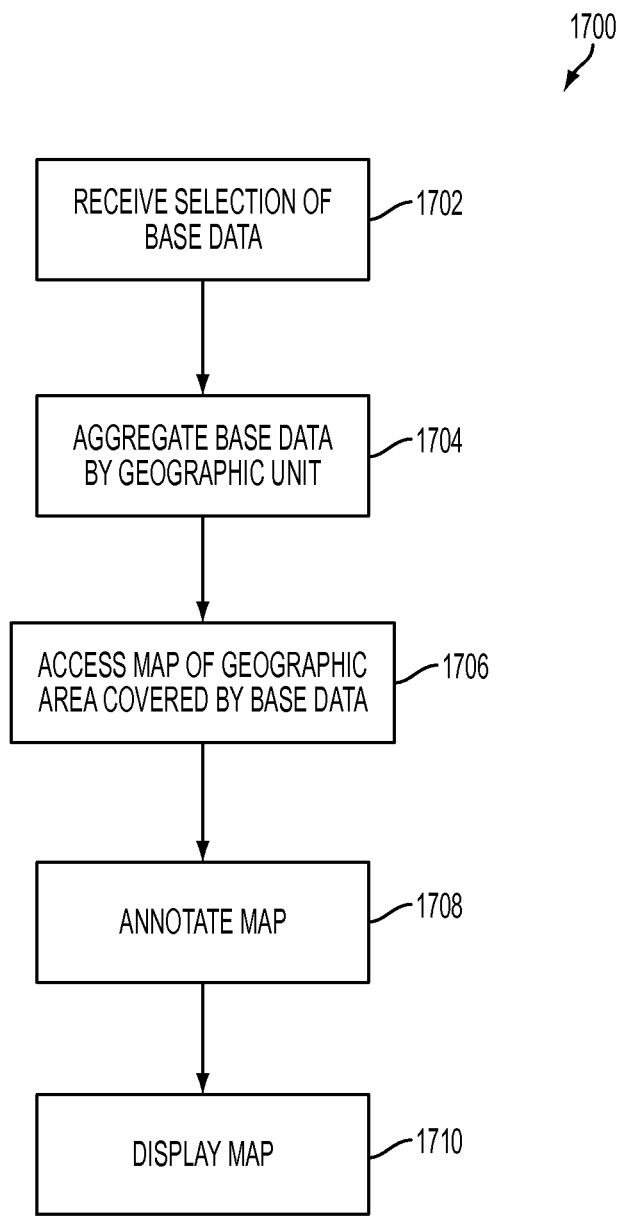
FIG. 17 describes a process for visualizing base data in a geographic context.

FIG. 17 describes a process 1700 for visualizing base data in a geographic context. The process 1700 begins with step 1702. At step 1702, a system such as, for example, the geographic analytics system 1606 of FIG. 16, receives a selection of base data from, for example, a client computer from the one or more client computers 1602 of FIG. 16. The selection of base data may be received via, for example, the analytics application operating on the at least one server computer 1608 of FIG. 16. The selection of base data typically identifies a data set of interest and includes at least one analytic metric of interest. From step 1702, the process 1700 proceeds to step 1704.

At step 1704, the geographic analytics system 1606 aggregates the selected base data by geographic unit such as, for example, ZIP code, city, county, state, or other geographic unit of interest. From step 1704, the process 1700 proceeds to step 1706. At step 1706, the at least one server computer 1708 accesses a map from the map repository 1658 that corresponds to a geographic region covering the aggregated base data. From step 1706, the process 1700 proceeds to step 1708.

At step 1708, the at least one server computer annotates the map with information from the aggregated base data, thereby illustrating geographic variance of the at least one analytic metric. From step 1708, the process 1700 proceeds to step 1710. At step 1710, the at least one server computer 1608 transmits the map as annotated to the client computer for display. After step 1710, the process 1700 ends.

Figure 18:
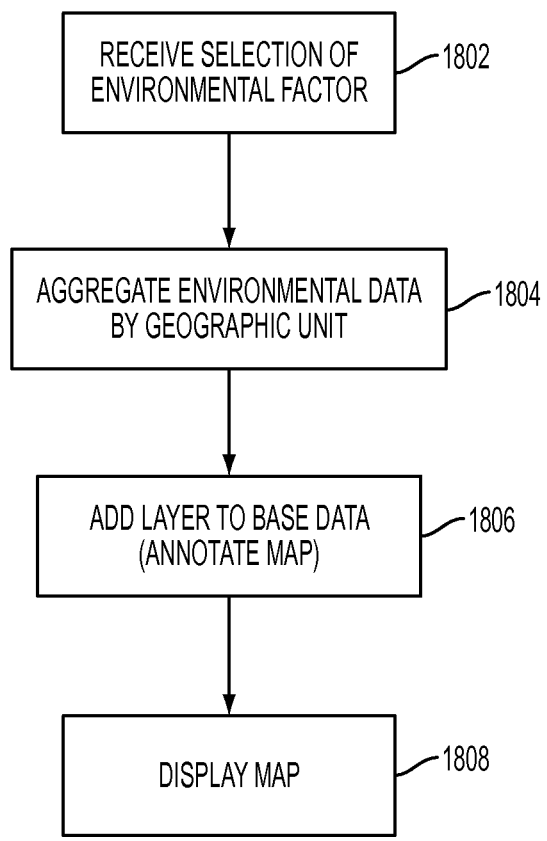
FIG. 18 describes a process for generating and visualizing new layers of information for base data.

FIG. 18 describes a process 1800 for generating and visualizing new layers of information for base data. In a typical embodiment, the process 1800 is performed either subsequent to or in tandem with the process 1700 of FIG. 17. The process 1800 begins at step 1802. At step 1802, a system such as, for example, the geographic analytics system 1606 of FIG. 1A, receives a selection of at least one environmental factor from a client computer from the one or more client computers 1602 of FIG. 16. The at least one environmental factor relates to the selected base data from step 1702 of FIG. 17. From step 1802, the process 1800 proceeds to step 1804.

At step 1804, the geographic analytics system 1606 aggregates environmental data for the at least one environmental factor by geographic unit. For example, if the base data is sales data for particular customers, the at least one environmental factor could relate to household income. Therefore, household-income data could be aggregated by a geographic unit such as, for example, ZIP code.

From step 1804, the process 1800 proceeds to step 1806. At step 1806, a new layer is added to the base data. Specifically, the aggregated environmental data is cross-referenced with the selected base data and correlated to a map from the map repository 1658. In general, each environmental factor may be considered a new layer of information related to the selected base data. The map with which the aggregated environmental data is correlated may be, for example, the map that was accessed during the process 1700. In that way, the at least one environmental factor becomes a new layer on the base data. In various embodiments, the map may be annotated with just the aggregated environmental data or together with the aggregated base data to create a composite map. From step 1806, the process 1800 proceeds to step 1808. At step 1808, the at least one server computer 1608 transmits the map to the client computer for display. After step 1808, the process 1800 ends.

An example of base data that can include geographic information is data related to patient encounters with healthcare providers. In various embodiments, patients have patient encounters with numerous healthcare providers including, but not limited to, clinics, hospitals, and other medical facilities. Healthcare providers usually independently maintain patient-encounter data for current and former patients for purposes of medical recordkeeping. The patient-encounter data may be stored and maintained to facilitate, for example, future provision of services, billing or evaluative functions, or other functions. The patient-encounter data may include, for example, addresses and ZIP codes for patients.

To help fully convey various inventive principles to one of ordinary skill in the art, FIGS. 1A-15 and 19-21 provide specific examples related to patient-encounter records in the healthcare industry. It should be appreciated that these examples are not limiting and that the principles described herein may be applied to other situations involving base data that includes geographic information.

FIGS. 1A-4 describe a patient index system that receives and links patient-encounter (PE) records to create base data, sometimes referenced herein as patient-encounter data or patient records. FIGS. 5-15 illustrate an exemplary system and processes for generating analytics using a patient index system. Finally, FIGS. 19-21 describe an exemplary system and processes for generating geographic analytics using base data from a patient index system.

For purposes of the healthcare examples discussed below, a patient encounter involves the provision of medical services to a person (i.e., a patient) by a healthcare provider. For instance, a patient encounter may be an outpatient encounter at a clinic or hospital for purposes of medical diagnosis or treatment. A patient encounter may also be an inpatient encounter, for example, at a hospital or other inpatient facility.

Patient-encounter (PE) data, as used herein, is data about a patient encounter that is typically collected by the healthcare provider. Patient-encounter data may include, for example, information identifying the patient, information identifying the healthcare provider, information identifying any medical services provided, information identifying any medical diagnoses made, and other similar medical information. Data about a particular patient encounter may be referred to herein as a patient-encounter (PE) record. Any record about a patient, whether or not a PE record, may be referred to herein as a patient record.

Figure 1A:
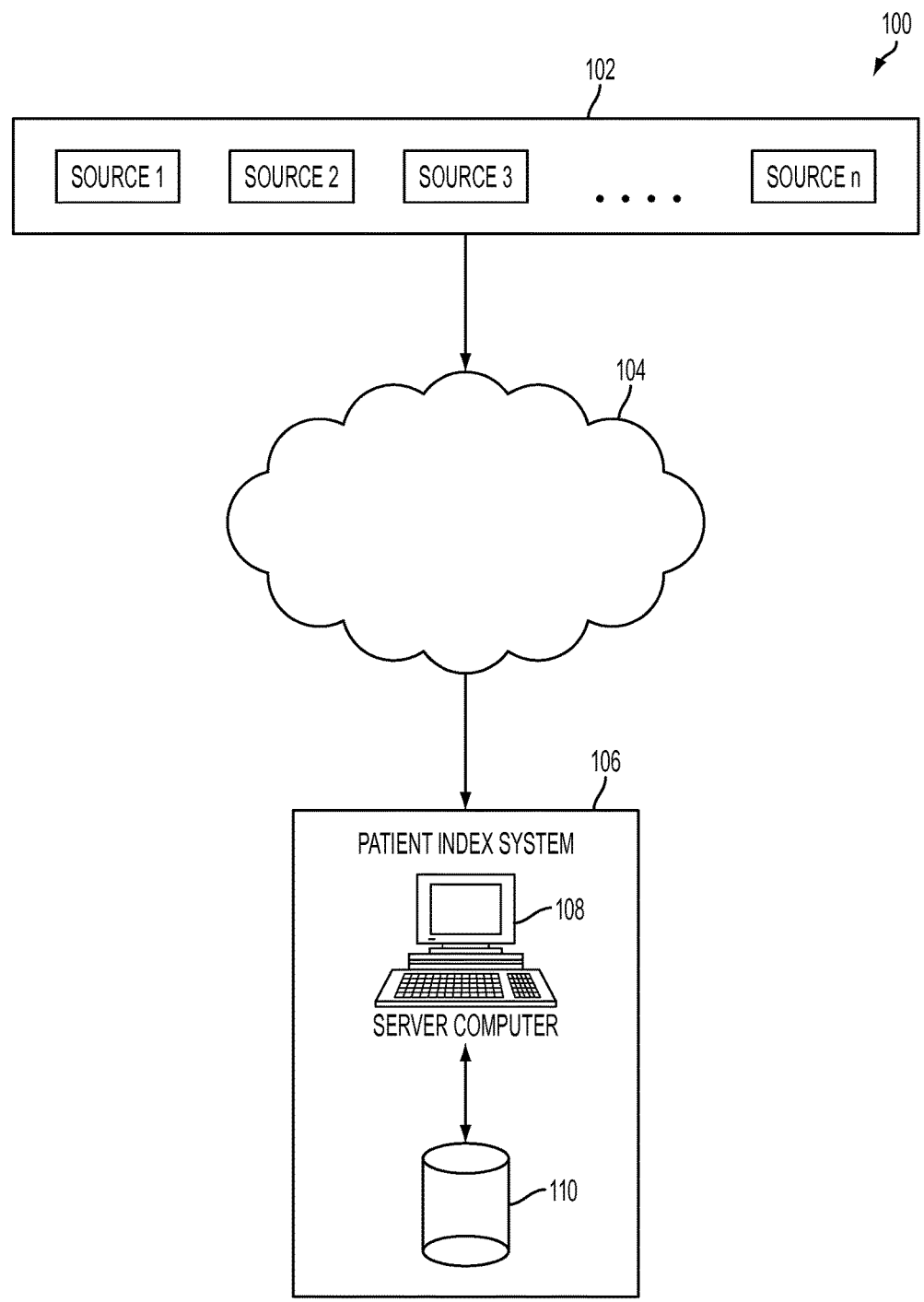
FIG. 1A illustrates a system for inputting and linking PE records from disparate sources.

FIG. 1A illustrates a system 100 for inputting and linking PE records from disparate sources. The system 100 includes a plurality of PE sources 102 that each generate or store PE data. Each PE source 102 in the plurality of PE sources 102 may generally be considered to be a computer system for a healthcare provider or for an institution that maintains PE data on behalf of a healthcare provider. The plurality of PE sources 102 communicate over a network 104 with a patient index system 106 to provide PE records. The network 104 may be, for example, the Internet. The patient index system 106 includes at least one server computer 108 and a data warehouse 110.

One of ordinary skill in the art will appreciate that the at least one server computer 108 is exemplary in nature and is shown in order to describe various inventive features to one of ordinary skill in the art. The patient index system 106 may utilize any number of physical or virtual server computers to perform any functionality described herein with respect to the at least one server computer 108 or the patient index system 106. The data warehouse 110 is similarly exemplary in nature. After reviewing the inventive principles described herein, one of ordinary skill in the art will appreciate that a given implementation of the patient index system 106 may utilize more or fewer databases to achieve similar functionality.

An objective of the patient index system 106 is to non-redundantly represent each patient for whom the data warehouse 110 stores patient records. In a typical embodiment, the patient index system 106 assigns a patient identifier (hereinafter, "PID") to each unique patient that is identified. The PID is typically a primary key for a master patient record for that patient. The patient index system 106 and, in particular, the data warehouse 110, stores a collection of master patient records that identifies each unique patient.

The PID is typically a unique number that bears no inherent relationship to a given patient's personal data. In this way, PID may be considered a non-sensitive identifier that can identify a unique patient in a de-identified manner. De-identification will be described in greater detail with respect to FIGS. 5-6. The data warehouse 110 typically uses the PID as a primary key for each patient and associates incoming PE records, for example, from the plurality of PE sources 102, with an appropriate PID.

In a typical embodiment, the incoming PE records are received from the plurality of PE sources 102 over the network 104 according to a predetermined data structure. Exemplary types of fields that may be included in PE records are described with respect to FIG. 1B. The incoming PE records may originate from, for example, insurance claims, clinical reports, discharge reports, or any other document reporting on patient encounters. The incoming PE records are associated with an appropriate PID via utilization of linking rules.

Errors and incomplete information on medical records can be as commonplace as medical records are voluminous. Data-entry errors and/or missing information frequently result in incorrect names, SSNs, and other information being included in PE records. In a typical embodiment, linking rules help address the problem of inaccurate or incomplete information in PE records. Linking rules specify criteria for determining whether one patient record should be linked to another patient record (i.e., because the records relate to the same person), even if some data elements do not exactly match. Linking rules evaluate to a Boolean result. As a result, patient records (e.g., PE records) that would otherwise be considered to refer to distinct patients may instead be correctly stored with respect to a PID for a particular patient to whom they correspond.

In various embodiments, the plurality of PE sources 102 may correspond to a logical grouping of healthcare providers based on at least one common denominator. For example, the plurality of PE sources 102 can correspond to healthcare providers from a same geographic region. The same geographic region may be, for example, a same city, metropolitan area, state, country, or other geographic division. In various embodiments, logically grouping in this fashion can have the benefit of tracking patients across multiple healthcare providers for the geographic region. In that way, encounter data maintained by the data warehouse 110 is enriched and made more comprehensive for an overlapping set of patients. As a result, patients can be tracked across time, payers, and healthcare providers.

Figure 1B:
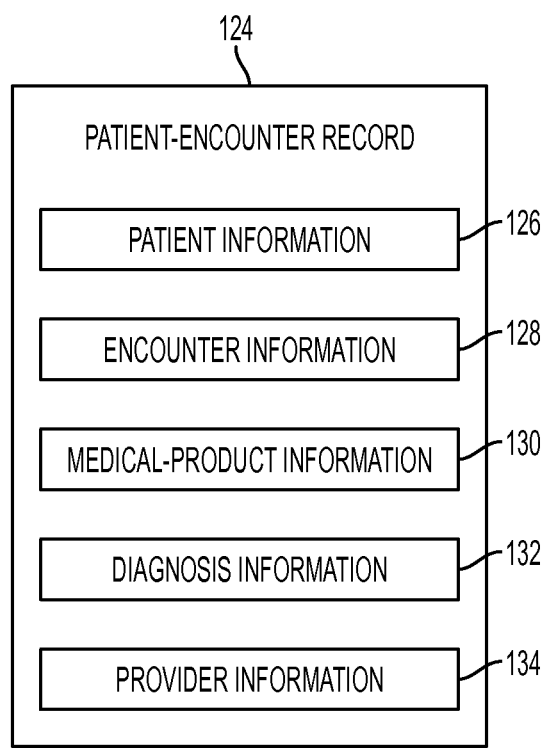
FIG. 1B illustrates exemplary data that may be included in a PE record.

FIG. 1B illustrates exemplary data that may be included in a PE record. In particular, a PE record 124 for an encounter is illustrated. The PE record 124 includes patient information 126, encounter information 128, medical-product information 130, diagnosis information 132 and healthcare-provider information 134. It should be appreciated that FIG. 1B illustrates examples of information that may be included in PE records. In a given implementation, a particular PE record may include more, less, or different information from that shown for the PE record 124.

The patient information 126 generally encompasses information that may be used to identify, contact, or classify a patient. The patient information 126 may include fields defined to store data such as, for example, first name, middle name, last name, date of birth (DOB), gender, social security number (SSN), physical or mailing address, phone number, and other similar personal information. The patient information 126 may also include, for example, ethnicity, race, state, county, and ZIP code. If, for example, the PE record 124 is based on claim data, the patient information 126 may also include the patient's payer information such as, for example, primary and/or secondary payers (e.g., insurance company name), policy number, etc. As described in greater detail with respect to FIG. 2, the patient information 126 is used during the application of linking rules to sets of PE records.

The encounter information 128 includes information that describes a type and a timing of the encounter. For example, the encounter information 128 includes a field for an encounter ID and fields that specify whether the encounter is an inpatient encounter or an outpatient encounter. The encounter information 128 also includes information about a date on which the encounter occurred. If the encounter is an inpatient encounter, the encounter information may specify, for example, a date of admission, a date of discharge, and a discharge disposition (e.g., died in hospital, discharged against medical advice, standard discharge, etc.). In a typical embodiment, both inpatient and outpatient encounters can be linked to a PID.

The medical-product information 130 lists medical products provided by the healthcare provider to the patient. So, the medical-product information 130 typically describes a medical good or service that the healthcare provider has provided the patient. The medical good or service may be, for example, open-heart surgery, hip-replacement surgery, etc.

To help describe the medical products, in various embodiments, each medical product in the medical-product information may be described by a standard code such as, for example, a diagnosis-related group (DRG) code, that corresponds to a particular medical product. Then, for each medical product, the medical-product information can further include a name, for example, of a physician or medical professional that performed or supplied the medical product, as applicable. In addition, for each medical product, the medical-product information can also include total charges by the healthcare provider for that medical product.

The diagnosis information 132 includes information about a diagnosis made in connection with the encounter. For example, particularly in the case of inpatient encounters, the diagnosis information 132 may include a primary diagnosis and, if applicable, one or more secondary diagnoses. To help efficiently describe diagnoses, in a typical embodiment, each diagnosis (whether primary or secondary) is described by a standard code such as, for example, an International Classification of Diseases (ICD) code (e.g., ICD-9, ICD-10, ICD-11, etc.).

The healthcare-provider information 132 includes information that identifies the healthcare provider for the encounter. The healthcare-provider information 132 may include, for example, a name and address, a provider-identification number, or the like. In a typical embodiment, the healthcare-provider information 132 includes information sufficient to cross-reference with other data for purposes of identifying, as applicable, the healthcare provider, ownership for the healthcare provider, a system group for the healthcare provider (e.g. a system group of hospitals), etc.

Figure 2:
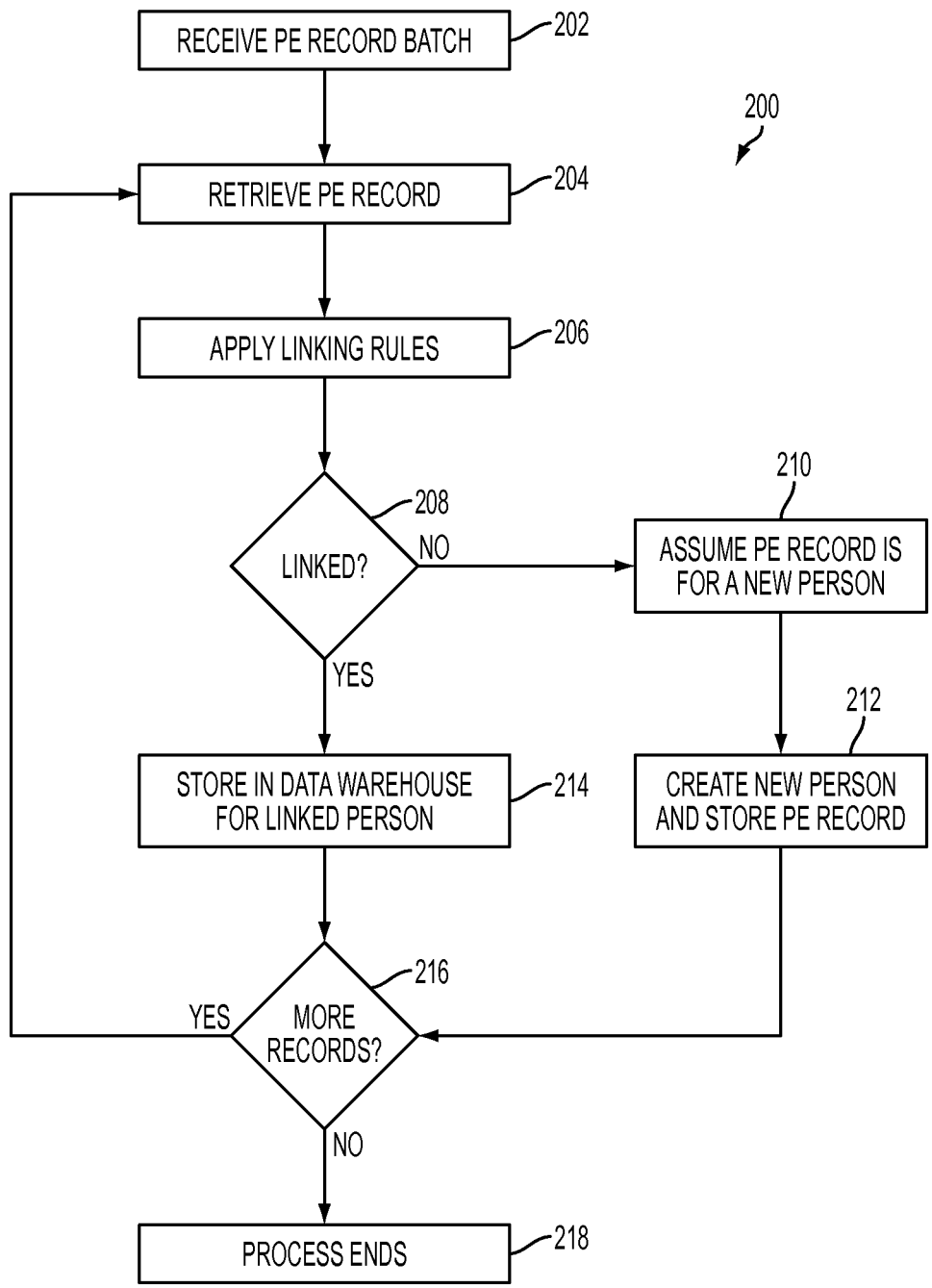
FIG. 2 illustrates a linking process.

FIG. 2 illustrates a linking process 200 that may utilize, for example, the system 100 of FIG. 1A. The linking process 200 begins at step 202. At step 202, the patient index system 106 receives a batch of PE records from one or more of the plurality of PE sources 102. The batch typically includes at least one PE record and may be loaded, for example, into a staging database. In various embodiments, batches of PE records are received at regular intervals such as, for example, quarterly. In various other embodiments, batches of PE records are received ad hoc. From step 202, the process 200 proceeds to step 204. At step 204, the patient index system 106 retrieves a PE record from the batch. From step 204, the process 200 proceeds to step 206.

At step 206, the patient index system 106 applies a set of linking rules to the retrieved PE record. In various embodiments, the patient index system 106 may apply all linking rules in the set of linking rules even once a linking rule in the set of linking rules reaches a Boolean result of "true." In various other embodiments, as a performance enhancement, the patient index system 106 may stop applying the set of linking rules once the Boolean result of "true" is reached. From step 206, the linking process 200 proceeds to step 208.

At step 208, the patient index system 106 determines whether the application of the set of linking rules at step 206 has resulted in the retrieved PE record being linked to a single master patient record (i.e., PID) in the data warehouse 110. In other words, at step 208, the patient index system 106 determines whether a Boolean result of "true" has been garnered for any master patient record (i.e., PID). If so, the retrieved PE record is stored in the data warehouse 110 for that PID. From step 208, the process 200 proceeds to step 214.

If at step 208 no master patient record has garnered a Boolean result of "true" for any linking rule in the set of linking rules, the linking process 200 proceeds to step 210. At step 210, the patient index system 106 assumes that the PE record is for a new patient that is not currently represented in the data warehouse 110. From step 210, the linking process 200 proceeds to step 212. At step 212, the patient index system 106 creates a new PID and master patient record in the data warehouse 110. The patient index system 106 stores the retrieved PE record with respect to the new PID. From step 212, the process 200 proceeds to step 214.

At step 214, the patient index system 106 determines whether more PE records remain in the batch. If so, the process 200 returns to step 204 to retrieve the next PE record. If no more PE records remain in the batch, the process 200 proceeds to step 218. At step 218, the process 200 ends.

Figure 3:
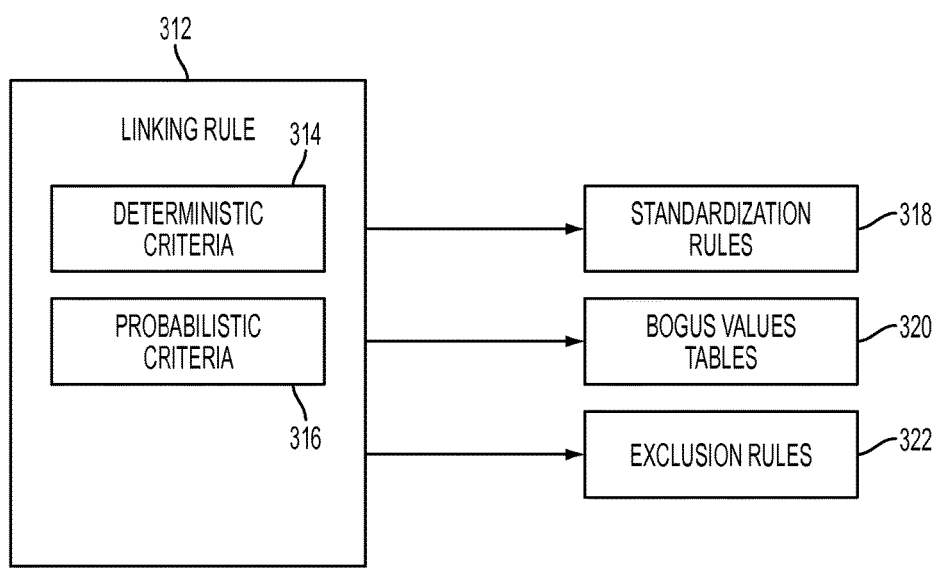
FIG. 3 illustrates a linking rule.

FIG. 3 illustrates a linking rule 312. The linking rule 312 includes deterministic criteria 314 and probabilistic criteria 316 for determining whether a first patient record should be linked to a second patient record (e.g. master patient record). In general, both the deterministic criteria 314 and the probabilistic criteria 316 must be satisfied for the linking rule 312 to evaluate to "true." As described in greater detail below, the linking rule may reference one or more standardization rules 318, one or more bogus values tables 320, and one or more exclusion rules 322. The one or more standardization rules 318, the one or more bogus values tables 320, and the one or more exclusion rules 322 are usually field-specific rather than linking-rule-specific. Thus, the one or more standardization rules 318, the one or more bogus values tables 320, and the one or more exclusion rules 322 may be applicable to any linking rule utilizing specified fields.

In a typical embodiment, the deterministic criteria 314 specify a subset of fields from the first patient record and the second patient record that, if matched (e.g., exactly matched), result in the deterministic criteria 314 being satisfied. For each field specified by the deterministic criteria 314, one of the standardization rules 318 may normalize the data contained therein for comparison purposes. For instance, one of the standardization rules 318 may mandate removal of punctuation characters such as hyphens, spaces, periods, and apostrophes. By way of further example, one of the standardization rules 318 may mandate that differences in case be ignored. As noted above, the one or more standardization rules 318 may be applicable to specific fields rather than specific linking rules. Thus, the one or more standardization rules 318 may be applicable to any linking rules utilizing those specific fields.

Furthermore, a table from the bogus values tables 320 may specify field values that, if present in a field specified by the deterministic criteria 314, prevent a match from being determined and cause the linking rule 312 to evaluate to "false." For example, for patients that are newborn babies, a common generic first name is "newborn." Therefore, if a PE record has a first name of "newborn," the linking rule can immediately be evaluated to reach a Boolean result of "false" and no linking can occur. As noted above, the bogus values tables 320 are generally applicable to specific fields rather than specific linking rules. Thus, the one or more bogus values tables 320 may be applicable to any linking rules utilizing those specific fields.

Additionally, for each field specified by the deterministic criteria 314, the one or more exclusion rules 322 may specify conditions that automatically cause a linking rule to evaluate to "false" and prevent linking based thereon. For example, in various embodiments, an exclusion rule from the one or more exclusion rules 322 may mandate that a name containing a number is not eligible for automatic linking via linking rules. It should be appreciated that the one or more bogus values tables 320 described above may also be considered a type of exclusion rule. As noted above, the one or more exclusion rules 322 are generally applicable to specific fields rather than specific linking rules. Thus, the one or more exclusion rules 322 may be applicable to any linking rules utilizing those specific fields.

In a typical embodiment, the probabilistic criteria 316 operate in conjunction with a demographics statistical tool that analyzes all fields from both the first and second patient records. In a typical embodiment, the demographics statistical tool provides a result to the patient index system that indicates a statistical weight (or confidence) that the first and second patient records refer to the same patient and should be linked. For example, in various embodiments, the statistical weight is value on a logarithmic scale such that values of fifteen or greater indicate a relatively high probability of a match, values of eight or greater and less than fifteen indicate a relatively moderate probability, and values below 8 indicate relatively low probability. In various embodiments, other scales and ranges may also be utilized. The probabilistic criteria 316 generally include a threshold value for the statistical weight or confidence. If the threshold value is not reached, the probabilistic criteria 316 are not satisfied.

Tables 1-10 below are examples of ten linking rules that may be utilized in various embodiments. In various embodiments, the ten linking rules in tandem are effective in linking patient records from disparate sources. Some of the linking rules below involve alias matching of names. Alias matching refers to identifying one name such as, for example, a first name, as an alias of another name. For example, the first names "Bill" and "William" may be determined to be an alias match.

TABLE 1

EXEMPLARY LINKING RULE NUMBER #1

DETERMINISTIC CRITERIA

| FIELD ON FIRST RECORD | CONDITION | FIELD ON SECOND RECORD | PROBABILISTIC CRITERIA |
|---|---|---|---|
| Last Name | EXACTLY MATCHES | Last Name | Weight >= 12 |
| First Name | EXACTLY MATCHES | First Name | |
| Date of Birth | EXACTLY MATCHES | Date of Birth | |
| Gender | EXACTLY MATCHES | Gender | |
| SSN | EXACTLY MATCHES | SSN | |

TABLE 2

EXEMPLARY LINKING RULE NUMBER #2

DETERMINISTIC CRITERIA

| FIELD ON FIRST RECORD | CONDITION | FIELD ON SECOND RECORD | PROBABILISTIC CRITERIA |
|---|---|---|---|
| First Name | EXACTLY MATCHES | Last Name | Weight >= 12 |
| Last Name | EXACTLY MATCHES | First Name | |
| SSN | EXACTLY MATCHES | SSN | |
| Gender | EXACTLY MATCHES | Gender | |
| Date of Birth | EXACTLY MATCHES | Date of Birth | |

TABLE 3

EXEMPLARY LINKING RULE NUMBER #3

DETERMINISTIC CRITERIA

| FIELD ON FIRST RECORD | CONDITION | FIELD ON SECOND RECORD | PROBABILISTIC CRITERIA |
|---|---|---|---|
| First Name | EXACTLY MATCHES | Last Name | Weight >= 12 |
| Last Name | EXACTLY MATCHES | First Name | |
| Gender | EXACTLY MATCHES | Gender | |
| Date of Birth | EXACTLY MATCHES | Date of Birth | |
| Phone Number (OR Address) | EXACTLY MATCHES | Phone Number (OR Address) | |

TABLE 4

EXEMPLARY LINKING RULE NUMBER #4

DETERMINISTIC CRITERIA

| FIELD ON FIRST RECORD | CONDITION | FIELD ON SECOND RECORD | PROBABILISTIC CRITERIA |
|---|---|---|---|
| Gender | EXACT MATCH OF FEMALE | Gender | Weight >= 12 |
| First Name | EXACTLY MATCHES | First Name | |
| Date of Birth | EXACTLY MATCHES | Date of Birth | |
| SSN | EXACTLY MATCHES | SSN | |

TABLE 5

EXEMPLARY LINKING RULE NUMBER #5

DETERMINISTIC CRITERIA

| FIELD ON FIRST RECORD | CONDITION | FIELD ON SECOND RECORD | PROBABILISTIC CRITERIA |
|---|---|---|---|
| Gender | FEMALE ON BOTH | Gender | Weight >= 12 |
| First Name | EXACTLY MATCHES | First Name | |
| Date of Birth | EXACTLY MATCHES | Date of Birth | |
| Phone Number (OR Address) | EXACTLY MATCHES | Phone Number (OR Address) | |

TABLE 6

EXEMPLARY LINKING RULE NUMBER #6

DETERMINISTIC CRITERIA

| FIELD ON FIRST RECORD | CONDITION | FIELD ON SECOND RECORD | PROBABILISTIC CRITERIA |
|---|---|---|---|
| Last Name | EXACTLY MATCHES | Last Name | Weight >= 12 |
| First Name | EXACTLY MATCHES | First Name | |
| Gender | EXACTLY MATCHES | Gender | |
| Date of Birth | EXACTLY MATCHES | Date of Birth | |
| Phone Number (OR Address) | EXACTLY MATCHES | Phone Number (OR Address) | |

TABLE 7

EXEMPLARY LINKING RULE NUMBER #7

DETERMINISTIC CRITERIA

| FIELD ON FIRST RECORD | CONDITION | FIELD ON SECOND RECORD | PROBABILISTIC CRITERIA |
|---|---|---|---|
| Last Name | EXACTLY MATCHES | Last Name | Weight >= 12 |
| First Name | ALIAS MATCH | First Name | |
| Gender | EXACTLY MATCHES | Gender | |
| Date of Birth | EXACTLY MATCHES | Date of Birth | |
| SSN | EXACTLY MATCHES | SSN | |

TABLE 8

EXEMPLARY LINKING RULE NUMBER #8

DETERMINISTIC CRITERIA

| FIELD ON FIRST RECORD | CONDITION | FIELD ON SECOND RECORD | PROBABILISTIC CRITERIA |
|---|---|---|---|
| Last Name | EXACTLY MATCHES | Last Name | Weight >= 12 |
| First Name | ALIAS MATCH | First Name | |
| Gender | EXACTLY MATCHES | Gender | |
| Phone Number (OR Address) | EXACTLY MATCHES | Phone Number (OR Address) | |
| Date of Birth | EXACTLY MATCHES | Date of Birth | |

TABLE 9

EXEMPLARY LINKING RULE NUMBER #9

DETERMINISTIC CRITERIA

| FIELD ON FIRST RECORD | CONDITION | FIELD ON SECOND RECORD | PROBABILISTIC CRITERIA |
|---|---|---|---|
| Last Name | EXACTLY MATCHES | Last Name | Weight >= 20 |
| First Name | ALIAS MATCH | First Name | |
| Gender | EXACTLY MATCHES | Gender | |
| Phone Number (OR Address) | EXACTLY MATCHES | Phone Number (OR Address) | |
| SSN | EXACTLY MATCHES | SSN | |

TABLE 10

EXEMPLARY LINKING RULE NUMBER #10

DETERMINISTIC CRITERIA

| FIELD ON FIRST RECORD | CONDITION | FIELD ON SECOND RECORD | PROBABILISTIC CRITERIA |
|---|---|---|---|
| Last Name | NEITHER CONTAINS BABY ALIAS | Last Name | Weight >= 17 |
| First Name | NEITHER CONTAINS BABY ALIAS | First Name | |

TABLE 10-continued

EXEMPLARY LINKING RULE NUMBER #10

DETERMINISTIC CRITERIA

| FIELD ON FIRST RECORD | CONDITION | FIELD ON SECOND RECORD | PROBABILISTIC CRITERIA |
|---|---|---|---|
| Gender | EXACTLY MATCHES | Gender | |

Figure 4:
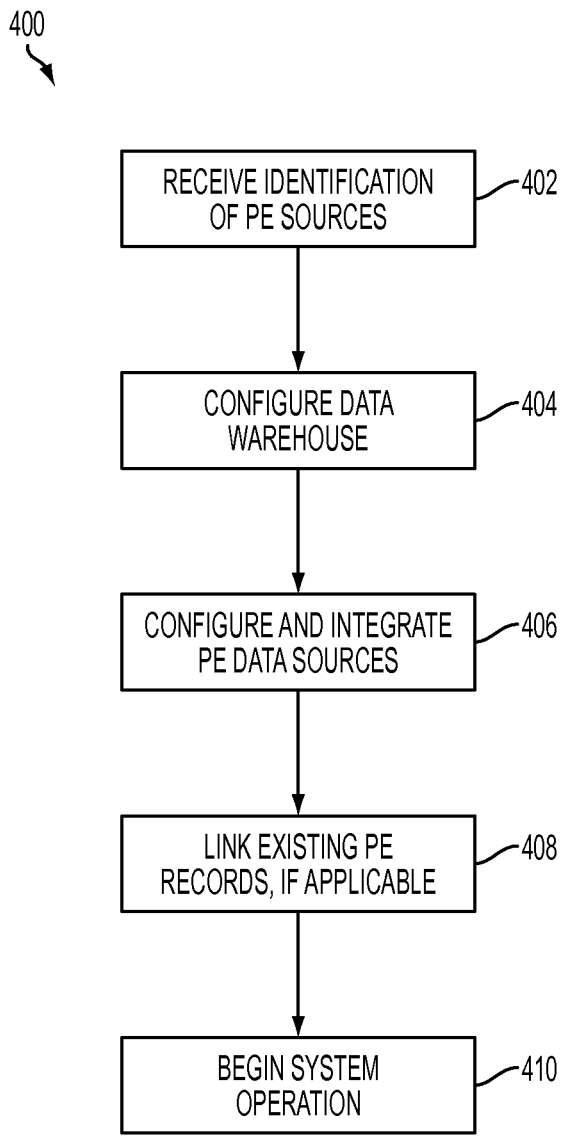
FIG. 4 illustrates a process for configuring a patient index system.

FIG. 4 illustrates a process 400 for configuring a patient index system such as, for example, the patient index system 106 of FIG. 1A, for particular implementations. The process 400 begins at step 402. At step 402, a patient index system such as, for example, the patient index system 106 of FIG. 1A, receives an identification of PE sources. In various embodiments, the identified PE sources may be a collection of computer systems that collectively serve, for example, all hospitals in a given region. From step 402, the process 400 proceeds to step 404.

At step 404, a data warehouse such as, for example, the data warehouse 110 of FIG. 1A, is configured. Configuration of the data warehouse typically entails configuring an overall data model. In a typical embodiment, the overall data model at least partially depends on a PE record data structure and a functional purpose of the patient index system. For example, if the PE sources will be providing claims (e.g., insurance claims), the PE record data structure (and the overall data model) will likely include fields that represent data usually present in claims. Furthermore, by way of example, if the primary functional purpose of the system is to generate analytics, the overall data model will likely include structures and attributes for generating whatever data is useful from an analytics standpoint. Examples of useful analytics will be described with respect to FIGS. 7-15. From step 404, the process 400 proceeds to step 406.

At step 406, the PE data sources are configured and integrated. For each PE data source, configuration of the PE data sources typically includes establishing settings necessary to transform the PE data source's raw PE data (e.g., claims, clinical records, etc.) into the PE record data structure. The settings may include, for example, translation rules. The integration of the PE data source typically includes, for example, establishing a connection with the data warehouse. From step 406, the process 400 proceeds to step 408.

At step 408, any existing PE records (once transformed as described with respect to step 406) can be linked via a linking process similar to the linking process 200 of FIG. 2. In that way, the data warehouse can be initially populated with existing data that is transformed and linked to develop a non-redundant collection of master patient records with PIDs. From step 408, the process 400 proceeds to step 410. At step 410, operation of the patient index system can begin, for example, as described with respect to FIGS. 1-3. After step 410, the process 400 ends.

As described above with respect to FIGS. 1A-4, a data warehouse may be developed that stores comprehensive information related to patient encounters within, for example, a geographic region. In that way, despite the presence of multiple providers, payers, and diagnoses, patients can be tracked through time via received information about each patient encounter. In various embodiments, a data warehouse such as, for example, the data warehouse 106, can be used to generate information regarding trends within a region, trends for specific geographic subsections of a region, trends for specific disease models, practice patterns for operating positions, comorbidities analysis (e.g., other diagnoses that frequently accompany a diagnosis of interest), insurance payment analysis, payer analysis, and the like. Examples of analytics aspects of a patient index system such as, for example, the patient index system 110, will be described below.

Figure 5:
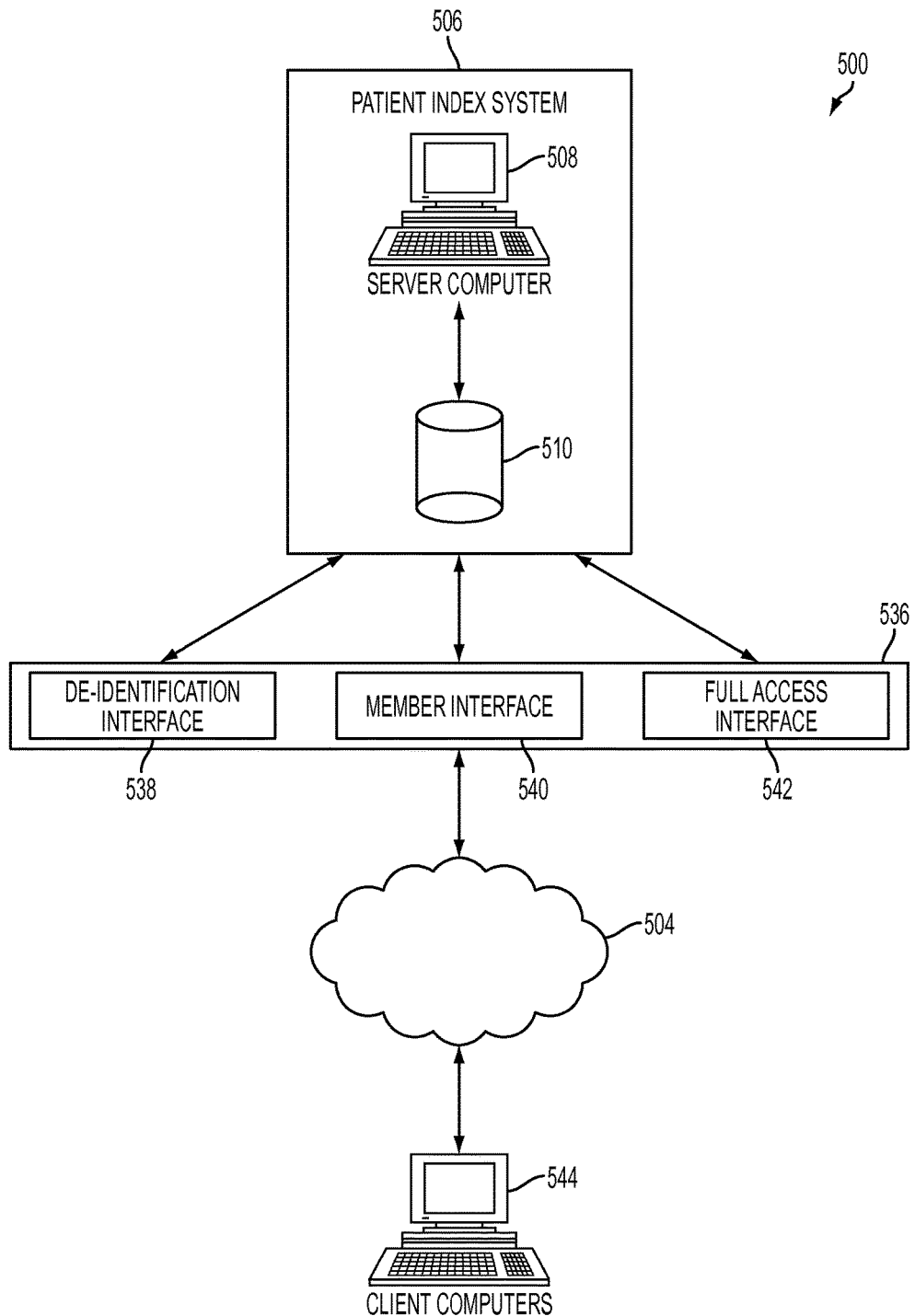
FIG. 5 illustrates a system for providing restricted access to a patient index system.

FIG. 5 illustrates a system 500 for providing restricted access to a patient index system. The system 500 includes a patient index system 506, an analytics interface 536, a network 504, and one or more client computers 544. In a typical embodiment, the patient index system 506 is comparable to the patient index system 106 of FIG. 1A and includes at least one server computer 508 and a data warehouse 510. The network 504 may be a computer network such as, for example, the Internet.

The analytics interface 536 provides the one or more client computers 544 with access to the patient index system 506. The analytics interface 536 may be, for example, a web interface, a remote-desktop interface into the at least one server computer 508, or another type of interface. In various embodiments, the analytics interface 536 provides at least three ways to access patient data stored in the data warehouse 510, namely: a de-identification interface 538, a member interface 540, and a full-access interface 542. The de-identification interface 538, the member interface 540, and the full-access interface 542 may be considered logical interfaces that illustrate that the at least three ways to access patient data in the data warehouse 510. These three interfaces will be described in greater detail below. In various embodiments, additional logical interfaces may also be provided in order to further vary how the data warehouse 510 is accessed.

The de-identification interface 538 is a logical interface that provides access to de-identified patient data from the data warehouse 510. As used herein, de-identified patient data is patient data that is sanitized in some manner so as to restrict one's ability to associate the patient data with a real-world person. A user accessing the de-identification interface 538 may be, for example, a medical researcher.

In a typical embodiment, the de-identification interface 538 is configurable based on preferences, security needs, or applicable law. For example, in the United States, the Health Insurance Portability and Accountability Act of 1996 (HIPAA) stipulates, inter alia, that certain personal health information (PHI) cannot be shared with other organizations. Thus, in a typical embodiment, the de-identification interface 538 may be configured to comply with HIPAA. Exemplary ways to perform de-identification will be described with respect to FIG. 6.

The member interface 540 is a logical interface that illustrates how members of the system 500 access patient data in the data warehouse 510. As used herein, a member may be considered an entity that provides a PE data source such as, for example, one of the plurality of PE data sources 102 of FIG. 1A. The member interface 540 provides a member with access to that member's own patient data and analytics based on that patient data. With respect to any other patient data, the member interface 540 operates identically to the de-identification interface 538.

The full-access interface 536 is a logical interface that provides access to all patient data in the data warehouse 510 in an unrestricted manner. Typically, the full-access interface 536 is only available to select employees of an organization that maintains the patient index system 506.

In operation, the one or more client computers 544 attempt to access the patient index system 506 via the analytics interface 536. A user of the one or more client computers 544 will have to provide proper credentials for a user account (e.g., user name and password) to access the analytics interface 536. Once the proper credentials have been verified, the user will be provided with access to the data warehouse 510 via an appropriate interface. The user's account typically specifies which interface that user accesses. By default, users will generally be given access to the de-identification interface 538. As explained above, the member interface 540 is limited to representatives of members and the full-access interface 542 is limited to very select personnel of an organization that maintains the patient index system 506.

After the user has access to the patient index system 506, the user is enabled, for example, to perform queries on patient data (e.g., PE data) and to generate analytics from patient data. Examples of analytics that may be generated will be described with respect to the ensuing FIGURES.

Figure 6:
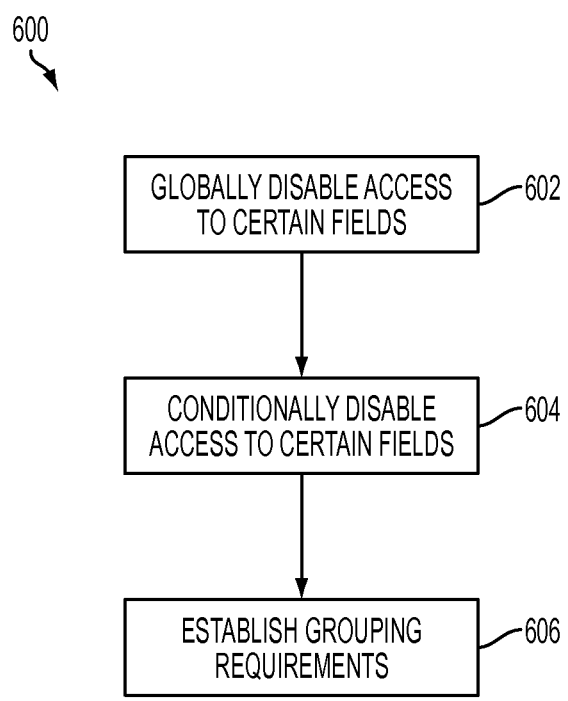
FIG. 6 illustrates an exemplary process for configuring a de-identification interface.

FIG. 6 illustrates an exemplary process 600 for configuring a de-identification interface such as, for example, the de-identification interface 538 of FIG. 5. It should be appreciated that the process 600 should not be viewed as limited to a list of sequential steps. Rather, in various embodiments, any step of the process 600 may be performed separate and apart from other steps of the process 600 for purposes of configuring the de-identification interface. The process 600 begins at step 602.

At step 602, access to certain fields is globally disabled across a data warehouse, such as, for example, the data warehouse 510 of FIG. 5. In that way, the globally disabled fields are not available for viewing or querying in any form. Typically, fields that are globally disabled are fields that are deemed not sufficiently ambiguous as to a patient, a healthcare provider, or both. In various embodiments, examples of fields that may be globally disabled are: a patent-encounter ID, a healthcare-provider ID, provider system name (e.g., hospital system name), account number, SSN, patient first name, patient last name, patient middle initial, patient date of birth, and patient address (except for ZIP code, which is not usually globally disabled). In various embodiments, many of the fields described with respect to the patient information 126 of FIG. 1B could be candidates for global disablement.

At step 604, access to certain other fields is conditionally disabled. Conditional disablement refers to disablement of fields for classes of patients that meet a particular condition (e.g., primary or secondary diagnosis of a particular disease). Conditional disablement is typically aimed at further protecting these classes of patients beyond what it is necessary to do on a global level. Also, classes of patients with certain diagnoses may exist in small enough numbers that even relatively generic fields such as, for example, a ZIP code, could make patients identifiable. For instance, in various embodiments, patients having a diagnosis of human immunodeficiency virus (HIV) or acquired immunodeficiency syndrome (AIDS) may have additional fields disabled. Diagnoses may typically be identified via diagnosis codes as described above with respect to FIG. 1B. Examples of fields that might be selected for conditional disablement are: ZIP code, gender, age, and ethnicity.

At step 606, in a manner similar to that described with respect to step 604, particular classes of patients may also be protected by establishing a grouping requirement. Grouping requirements stipulate that patient data for certain classes of patients may only be accessed as part of group (i.e., not individually at the patient level). For example, in various embodiments, a grouping requirement may be imposed on patients diagnosed with HIV or AIDS. Thus, although patient data might not be viewable individually at the patient level, it may be possible to view and analyze at least some patient data for these patients if the data is aggregated into a group such as, for example, patients from age 20-65.

In general, the scope of the grouping requirement may be: (1) all data fields for the particular classes of patients (that aren't globally disabled); or (2) some data fields for the particular classes of patients. In addition, depending on configuration, the grouping requirement may or may not override any conditional disablement as described with respect to step 604. If the grouping requirement overrides conditional disablement for some data fields, those data fields are available for viewing and analysis if aggregated into a group (e.g., by age, by 90-day period, etc.). To the extent the grouping requirement does not override conditional disablement for some data fields, those data fields are not available for viewing and analysis, even if aggregated into a group. Likewise, globally disabled fields are not generally available for viewing and analysis, even if aggregated into a group.

Because of the policy underlying grouping requirements, it is generally advantageous to aggregate patient data into large groups. Aggregating patient data into sufficiently large groups helps ensure dilution of that data by other data. In various embodiments, a predetermined threshold may be set to determine the sufficiently large group. The predetermined threshold may be, for example, a set number of patients meeting the criteria to fall within a group. After step 606, the process 600 ends.

Figure 7:
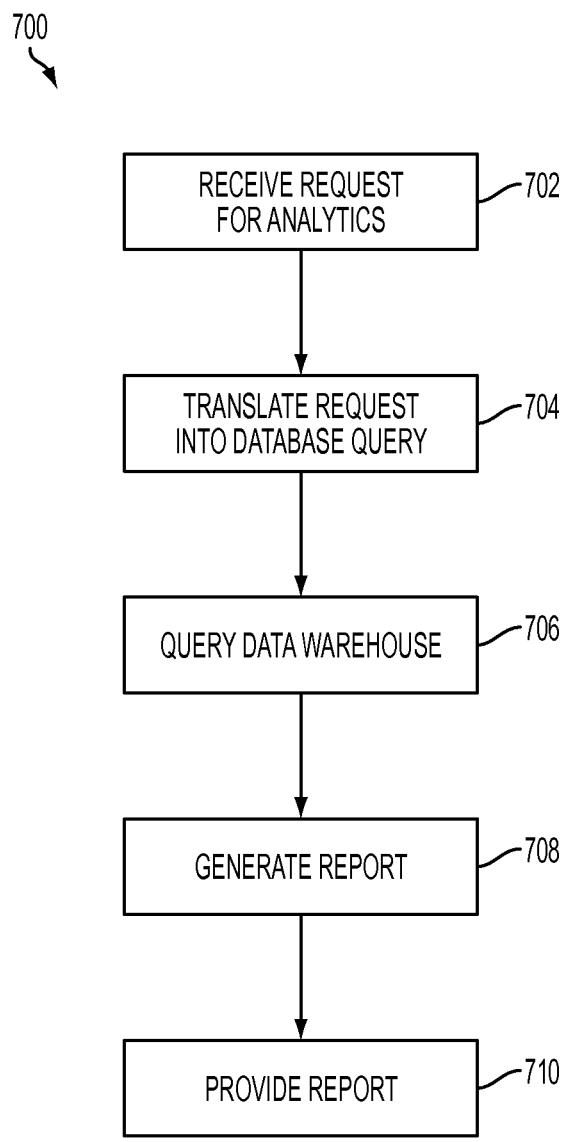
FIG. 7 illustrates a process for generating analytics.

FIG. 7 illustrates a process 700 for generating analytics using, for example, the system 500 of FIG. 5. As described above with respect to FIG. 5, the patient index system 506 includes patient data that allows patients to be tracked across time, payer, and healthcare provider (e.g., a hospital) for both inpatient and outpatient encounters. Thus, numerous analytics can be generated using data stored within a patient index system such as, for example, the patient index system 506 of FIG. 5. The process 700 begins with step 702.

At step 702, a server computer such as, for example, the at least one server computer 508 of FIG. 5, receives a request for analytics from, for example, a client computer. The request may specify, for example, at least one metric (i.e. field). The request may also optionally specify at least one variable (i.e. another field used to measure the at least one metric) and a data set to which the request is applicable (e.g., PE records having certain diagnosis codes as a primary diagnosis). For purposes of specifying the request, fields may be selected via an analytics interface such as, for example, the analytics interface 536 of FIG. 5 (as limited, e.g., by a de-identification interface). Exemplary formats for requests for analytics will be described with respect to FIGS. 8-10. From step 702, the process 700 proceeds to step 704.

At step 704, the server computer translates the request into one or more database queries. From step 704, the process 700 proceeds to step 706. At step 706, the server computer searches a data warehouse such as, for example, the data warehouse 510 of FIG. 5. From step 706, the process 700 proceeds to step 708. At step 708, the server computer generates a report using data retrieved via the query. In a typical embodiment, a format of the report may be specified as part of the request for analytics. From step 708, the process 700 proceeds to step 710. At step 710, the server computer provides the report to the client computer.

Figure 8:
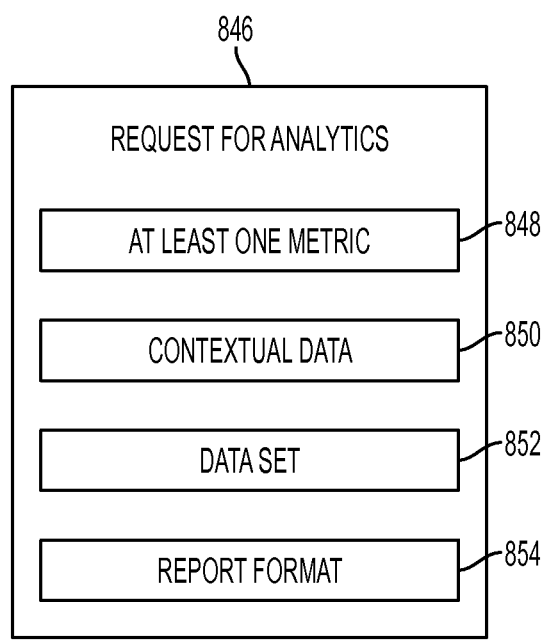
FIG. 8 illustrates an exemplary request for analytics.

FIG. 8 illustrates an exemplary request for analytics 846. The request for analytics specifies at least one metric 848, contextual data 850, a data set 852, and a report format. The at least one metric 848 is an analytical metric of interest to a requestor of analytics such as, for example, readmissions rate, readmissions count, lost reimbursement, and other metrics. In various embodiments, an analytics interface such as, for example, the analytics interface 536 of FIG. 5 can allow the at least one metric 848 to be selected. In some embodiments, the analytics interface may additionally allow the at least one metric 848 to be a custom metric that a requestor can specify in terms of a calculation using existing fields.

The contextual data 850 is data such as variables that can provide context or a basis for comparing values for the at least one metric. For example, the contextual data 850 may reference one or more disease models so that the at least one metric can be calculated and compared amongst the disease models. In a typical embodiment, a disease model may be defined by assigning a collection of applicable diagnose codes to particular diseases. Table 11 lists exemplary disease models and corresponding ICD codes. One of ordinary skill in the art will appreciate that many disease models can be specified.

TABLE 11

| EXEMPLARY DISEASE MODEL | EXEMPLARY ICD CODES |
| --- | --- |
| Congestive Heart Failure (CHF) | 402.01, 402.11, 402.91, 404.01, 404.03, 404.11, 404.13, 404.91, 404.93, 428.0, 428.1, 428.20, 428.21, 428.22, 428.23, 428.30, 428.31, 428.32, 428.32, 428.33, 428.40, 428.11, 4128.42, 428.43, 428.9 |
| Acute Myocardial Infarction (AMI) | 410.00, 410.01, 410.10, 410.11, 410.20, 410.21, 410.30, 410.31, 410.40, 410.41, 410.50, 410.51, 410.60, 410.61, 410.70, 410.71, 410.80, 410.81, 410.90, 410.91 |
| Pneumonia | 480.0, 480.1, 480.2, 480.3, 480.8, 480.9, 481, 482.0, 482.1, 482.2, 482.40, 482.31, 482.32, 482.39, 482.40, 482.41, 482.49, 482.81, 482.82, 482.83, 482.84, 482.89, 482.9, 483.0, 483.1, 483.8, 485, 486, 487 |

In a typical embodiment, the data set 852 represents patient records (e.g., master patient records) for which the at least one metric 848 and the contextual data 850 should be supplied. Therefore, the data set 852 typically includes limitations that define a data set of interest and hence a segment of a data warehouse that will be queried. Continuing the example in the preceding paragraph, the data set 852 may specify a certain patient zip code so that the at least one metric can be compared amongst a plurality of disease models for a specific zip code. The report format 854 specifies a format for reporting responsive to the request for analytics 846. For example, the report format 854 may be selectable from a list of report formats that are compatible with the request for analytics 846 (e.g., charts, graphs, tables, etc.).

With reference to FIGS. 1A and 5, in various embodiments, a patient index system may be implemented as a regional patient index system that serves hospitals throughout a given region. In this fashion, as described above, patients can be tracked across time, payers, and hospitals and comprehensive analytics may be generated for the region. An exemplary category of analytics relates to readmissions. Typically, a given inpatient encounter is considered either an initial admission or a readmission, but not both. In various embodiments, configurable rules are established to distinguish initial admissions and readmissions. For example, in some embodiments, a readmission is any admission of a patient that is within thirty days of a date of discharge for another admission of that patient. Continuing with the example, any other admission is an initial admission. In various embodiments, other periods of time may be substituted for the thirty-day time period as appropriate.

Figure 9:
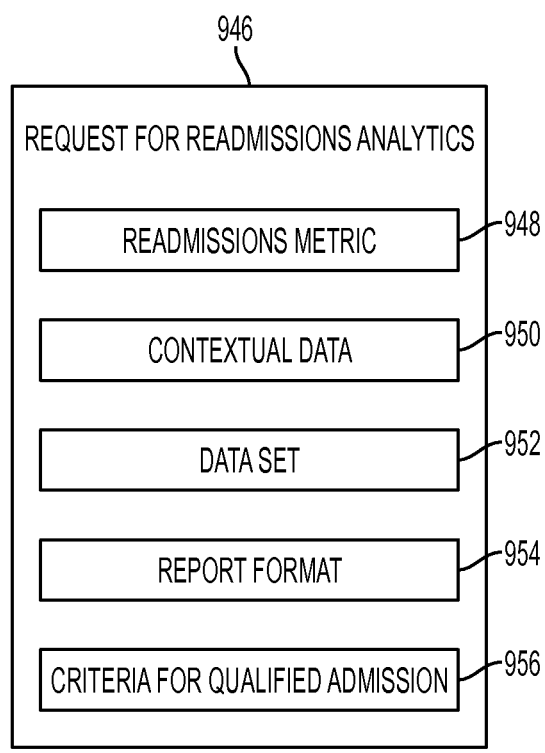
FIG. 9 illustrates a request for readmissions analytics.
Figure 10:
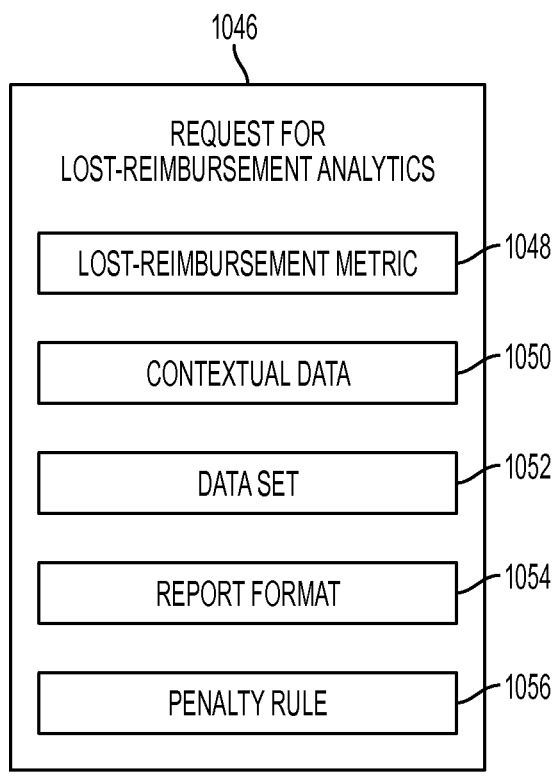
FIG. 10 illustrates a request for lost-reimbursement analytics.

An ongoing problem for hospitals is obtaining reimbursement for what are deemed by payers to be "preventable readmissions." For example, the Center for Medicare and Medicaid Services (CMS) recently promulgated a rule that it will not reimburse for readmissions of any hospital within thirty days of the discharge. At times, penalties, including non-reimbursement, may be imposed for readmissions related to specific illnesses such as, for example, chronic heart failure (CHF) and pneumonia. FIGS. 9-10 describe, through examples, how a patient index system such as, for example, the patient index system 506 of FIG. 5, can facilitate analytics related to readmissions and reimbursement penalties.

FIG. 9 illustrates a request for readmissions analytics 946. In a typical embodiment, readmissions analytics can be generated for a particular hospital (e.g., via a member interface) or, for example, for the entire region (e.g., via a de-identification interface). The request for readmissions analytics specifies at least one readmissions metric 948, contextual data 950, a data set 952, a report format 954, and criteria for a qualified admission 956. The contextual data 950, the data set 952, and the report format 954 are typically similar to the contextual data 850, the data set 852, and the report format 854, respectively, as described with respect to FIG. 8.

The at least one readmissions metric 948 may be, for example, a readmissions count or a readmissions rate. The readmissions count is a raw number of readmissions that meets all elements of the request for readmissions analytics 946. The readmissions rate is a percentage of all initial readmissions that are followed by at least one readmission (however readmissions are defined in a given implementation).

The criteria for qualified admissions 956 specifies which admissions should be considered for purposes of generating the at least one readmissions metric 948. In a typical embodiment, not all admissions are considered in calculating the at least one readmissions metric. Rather, often in accordance with rules and regulations set by payers, some admissions to hospitals may be excluded from being consideration. Admissions that satisfy the criteria for qualified admissions 956 by not being excluded may be considered qualified admissions.

In various embodiments, the criteria for qualified admissions 956 include exclusion rules that define which admissions should not be considered (i.e. not qualified). In various embodiments, an exclusion rule could be established that, if a discharge disposition from a hospital has one of a certain set of values, that admission is not a qualified admission. Examples of discharge dispositions that might exclude a particular admission from being considered a qualified admission are: died in hospital, discharged against medical advice, transferred to another acute facility. If the admission is not a qualified admission, then the admission cannot be considered an initial admission for purposes of deeming future admissions to be readmissions.

FIG. 10 illustrates a request for lost-reimbursement analytics 1046. The request for lost-reimbursement metrics specifies at least one lost-reimbursement metric 1048, contextual data 1050, a data set 1052, a report format 1054, and a penalty rule 1056. The contextual data 1050, the data set 1052, and the report format 1054 are typically similar to the contextual data 850, the data set 852, and the report format 854, respectively, as described with respect to FIG. 8. The at least one lost-reimbursement metric 1048 may be, for example, a metric, in U.S. currency, that reflects a cumulative result of one or more reimbursement penalties imposed by a payer.

The reimbursement penalty rule 1056 specifies a rule and a corresponding reimbursement penalty if the rule is met. The rule typically specifies conditions that result in the reimbursement penalty. The reimbursement penalty may specify, for example, a percentage reimbursement of readmission costs that will not be paid. By way of example, the reimbursement penalty rule 1056 could specify that readmission at any hospital within thirty days of discharge results in a one-hundred-percent penalty for the readmission (i.e., no reimbursement). At times, a hospital performing an initial admission and a hospital performing a readmission may be different hospitals. The hospital responsible for the initial admission may sometimes be assessed the penalty rather than the hospital performing the readmission. However, regardless of which hospital is assessed the reimbursement penalty, the net effect is the same when, for example, analyzing lost reimbursement across a region of hospitals.

Calculation of the at least one lost-reimbursement metric 1048 involves calculating lost reimbursement for each readmission subsumed within the data set 1052 and aggregating as necessary in accordance with the contextual data 1050. For a given readmission, lost reimbursement is an amount of reimbursement that was obtained subtracted from an amount of reimbursement that should have been obtained. Expressed another way, lost reimbursement is typically an amount of reimbursement that would have otherwise been obtained for services performed multiplied by the penalty (expressed as a percentage). Since services performed (medical products) are typically expressed in a data warehouse via DRG codes, the amount of reimbursement that would have otherwise been obtained can typically be determined by looking up a provider-specific reimbursement amount for each of the DRG codes and totaling. If a provider-specific reimbursement is not available, an average amount for the region may be utilized.

In various embodiments, readmissions and lost-reimbursement analytics such as those described above can be used as a basis to enact change for purposes of reducing readmissions and penalty-induced lost reimbursements. For example, with reference to disease models as described with respect to FIG. 8, it may be determined that readmissions rates following a primary diagnosis of chronic heart failure (CHF) (as defined by the disease model) is too high. Following that, a new treatment program may be implemented that results in a change in how patients with CHF as a primary diagnosis are treated during an initial admission. In such a situation, in various embodiments, it is advantageous to generate additional analytics regarding effects of the change, for example, on readmissions rates.

Figure 11:
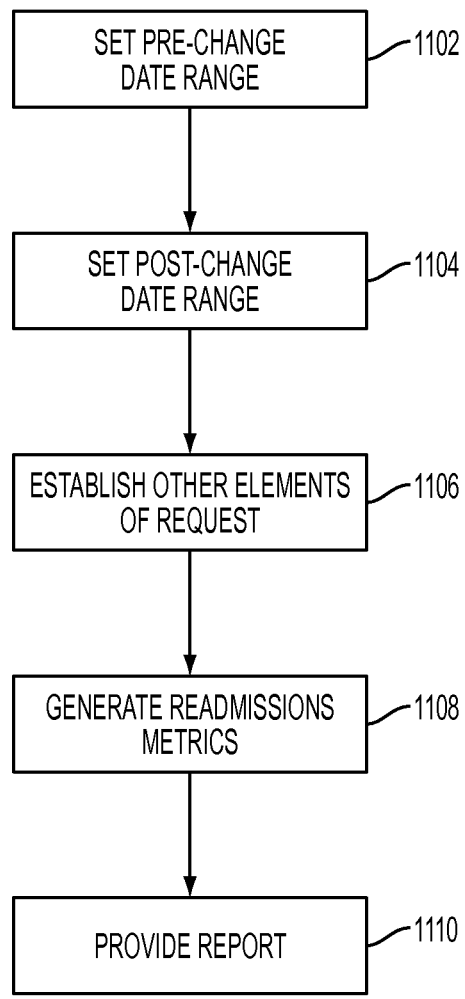
FIG. 11 illustrates a process for determining changes in analytics over time.

FIG. 11 illustrates a process 1100 for determining changes in analytics over time. The process 100 begins at step 1102. At step 1102, a patient index system such as, for example, the patient index system 506 of FIG. 5, sets a pre-change date range responsive to user input. The pre-change date range establishes a beginning date and an ending date for a period prior to the change. From step 1102, the process 1100 proceeds to step 1104. At step 1104, the patient index system sets a post-change date range responsive to user input. The post-change date range establishes a beginning date and an ending date for a period after the change. From step 1104, the process 1100 proceeds to step 1106.

At step 1106, other elements of a request for analytical data are established. For example, if performing a request for readmissions analytics, at least one metric (e.g., readmissions rate), contextual data, a data set, and a report format may be specified. From step 1106, the process 1100 proceeds to step 1108. At step 1108, the patient index system generates readmissions analytics for the pre-change date range and the post-change date range pursuant to the request. In a typical embodiment, the generation includes performing two queries of a data warehouse (e.g., the data warehouse 510 of FIG. 5), that is, one query for each of the pre-change date range and the post-change date range.

From step 1108, the process 1100 proceeds to step 1110. At step 1110, a report comparing the readmissions analytics for the pre-change date range and the post-change date range is provided, for example, to a requestor. After step 1110, the process 1100 ends.

In various embodiments, an advantage of a regional patient index system as described above is an ability to identify and analyze problems and issues across the region. For example, in various embodiments, the most common comorbidities within the region for specific diagnoses can be identified. Using this information regarding common comorbidities, better treatment and care can be provided within the region.

Figure 12:
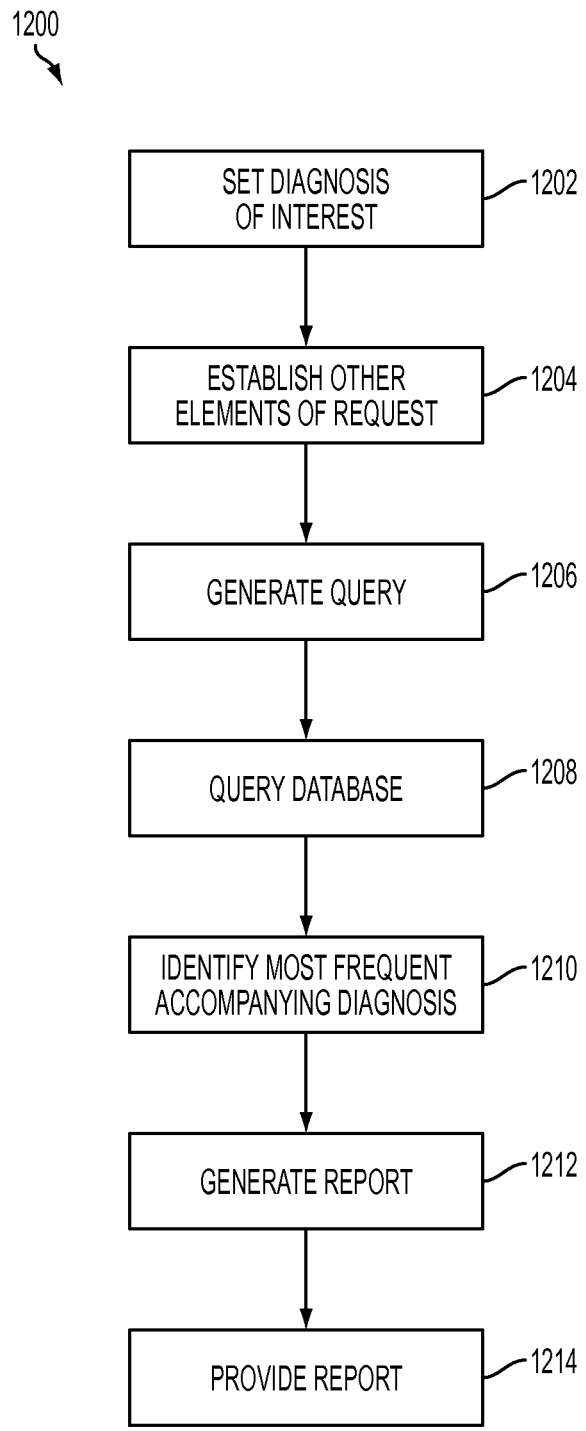
FIG. 12 illustrates a process for identifying most common comorbidities.

FIG. 12 illustrates a process 1200 for identifying the most common accompanying diagnoses for a particular diagnosis. The process 1200 begins with step 1202. At step 1202, a patient index system such as, for example, the patient index system 506 of FIG. 5, sets a diagnosis of interest responsive to user input. The diagnosis of interest may be, for example, a diagnosis that is represented by a diagnosis code or a collection of diagnosis codes. The diagnosis of interest may also be, for example, a disease model as described with respect to FIG. 8. From step 1202, the process 1200 proceeds to step 1204.

At step 1204, other elements of a request for analytical data are established. For example, contextual data, a data set, and a report format may be specified. From step 1204, the process 1200 proceeds to step 1206. At step 1206, the patient index system generates a query based on steps 1202 and 1204 that searches for diagnoses (primary or secondary) that accompany the diagnosis of interest. From step 1206, the process 1200 proceeds to step 1208. At step 1208, a data warehouse such as, for example, the data warehouse 510 of FIG. 5, is queried via the query. From step 1208, the process 1200 proceeds to step 1210.

At step 1210, the patient index system identifies the most numerous (e.g., five most numerous) accompanying diagnoses (i.e., comorbidities) for the diagnosis of interest set at step 1202. From step 1210, the process 1200 proceeds to step 1212. At step 1212, the patient index system generates a report containing the most numerous comorbidities in accordance with the report format. From step 1212, the process 1200 proceeds to step 1214. At step 1214, the report is provided to a requestor. After step 1214, the process 1200 ends.

Figure 13:
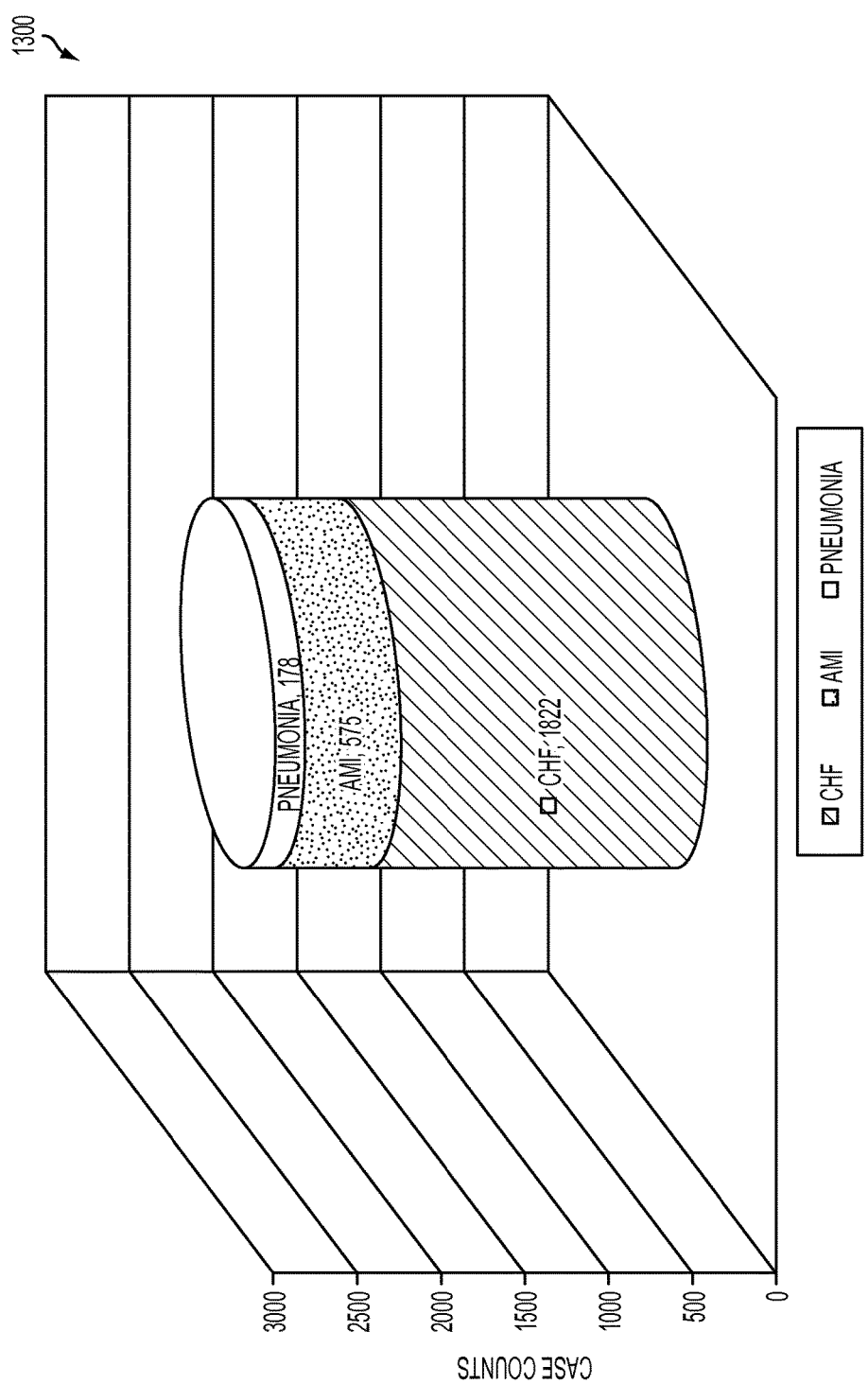
FIG. 13 illustrates a graph of readmission counts.
Figure 14:
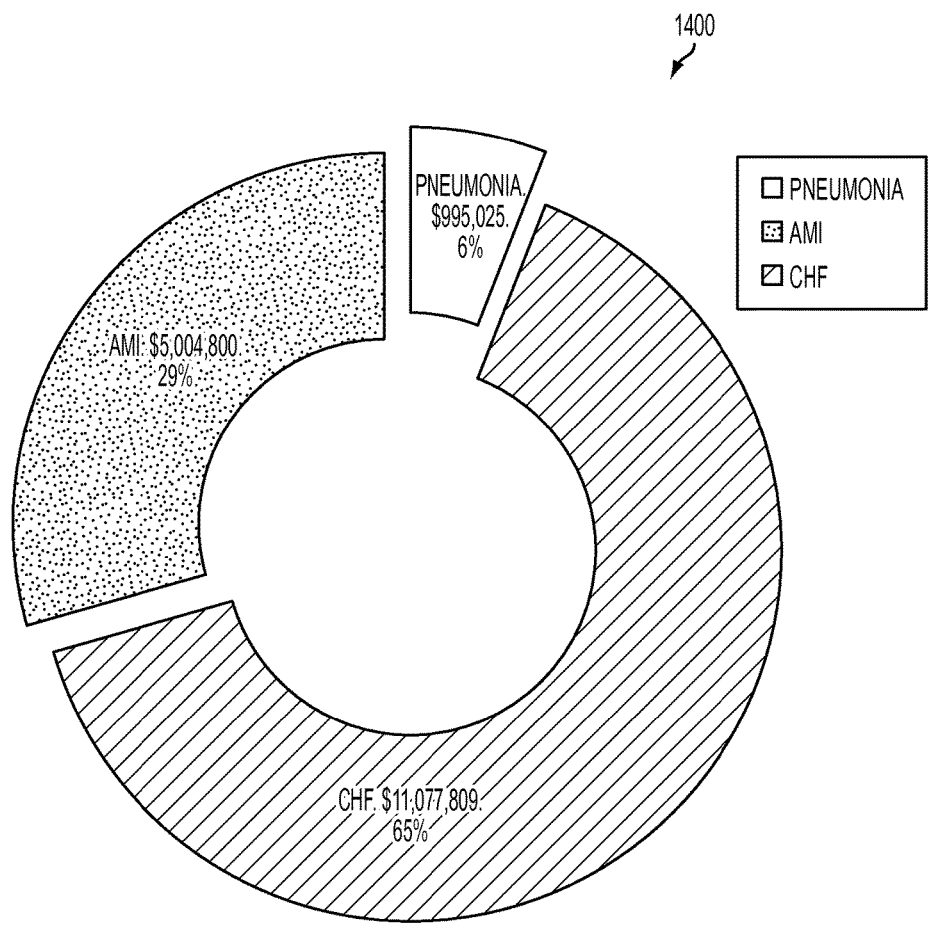
FIG. 14 illustrates a graph of reimbursement losses.
Figure 15:
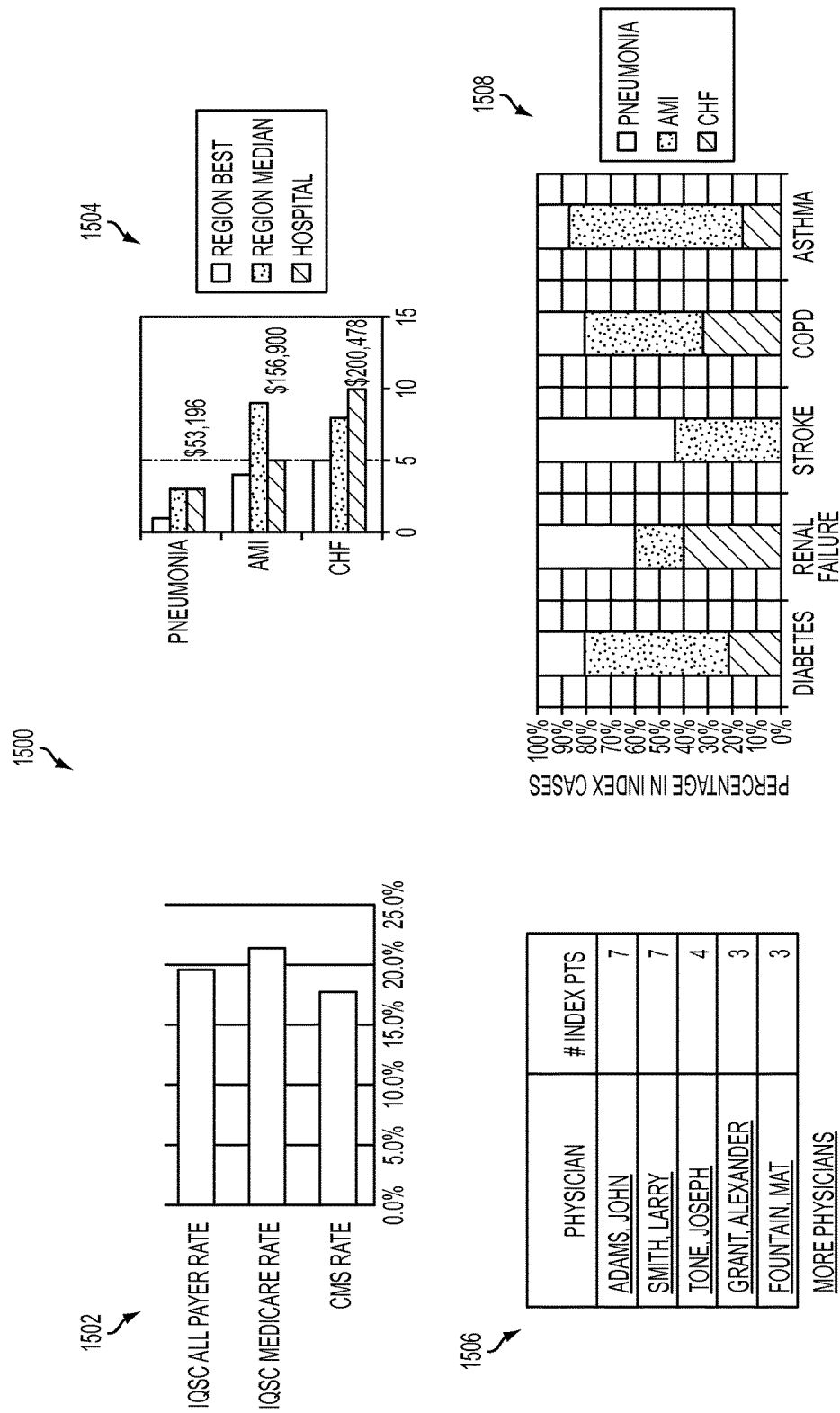
FIG. 15 illustrates an exemplary dashboard.

FIGS. 13-15 illustrate exemplary reports that may be generated via a patient index system such as, for example, the patient index system 506 of FIG. 5. FIG. 13 illustrates a graph 1300 of readmission counts. In particular, the graph 1300 compares readmission counts for disease models of pneumonia, AMI, and CHF.

FIG. 14 illustrates a graph 1400 of reimbursement losses by disease model. In particular, the graph 1400 compares lost reimbursements due to readmissions among disease models of pneumonia, AMI, and CHF.

FIG. 15 illustrates an exemplary dashboard 1500. In various embodiments, the dashboard 1500 is an example of a dashboard that may be provided upon log-in to a patient index system such as, for example, the patient index system 506 of FIG. 5. The dashboard 1500 includes a readmission-rate graph 1502, a reimbursement-loss graph 1504, a physician chart 1506, and a comorbidities graph 1508.

Figure 19:
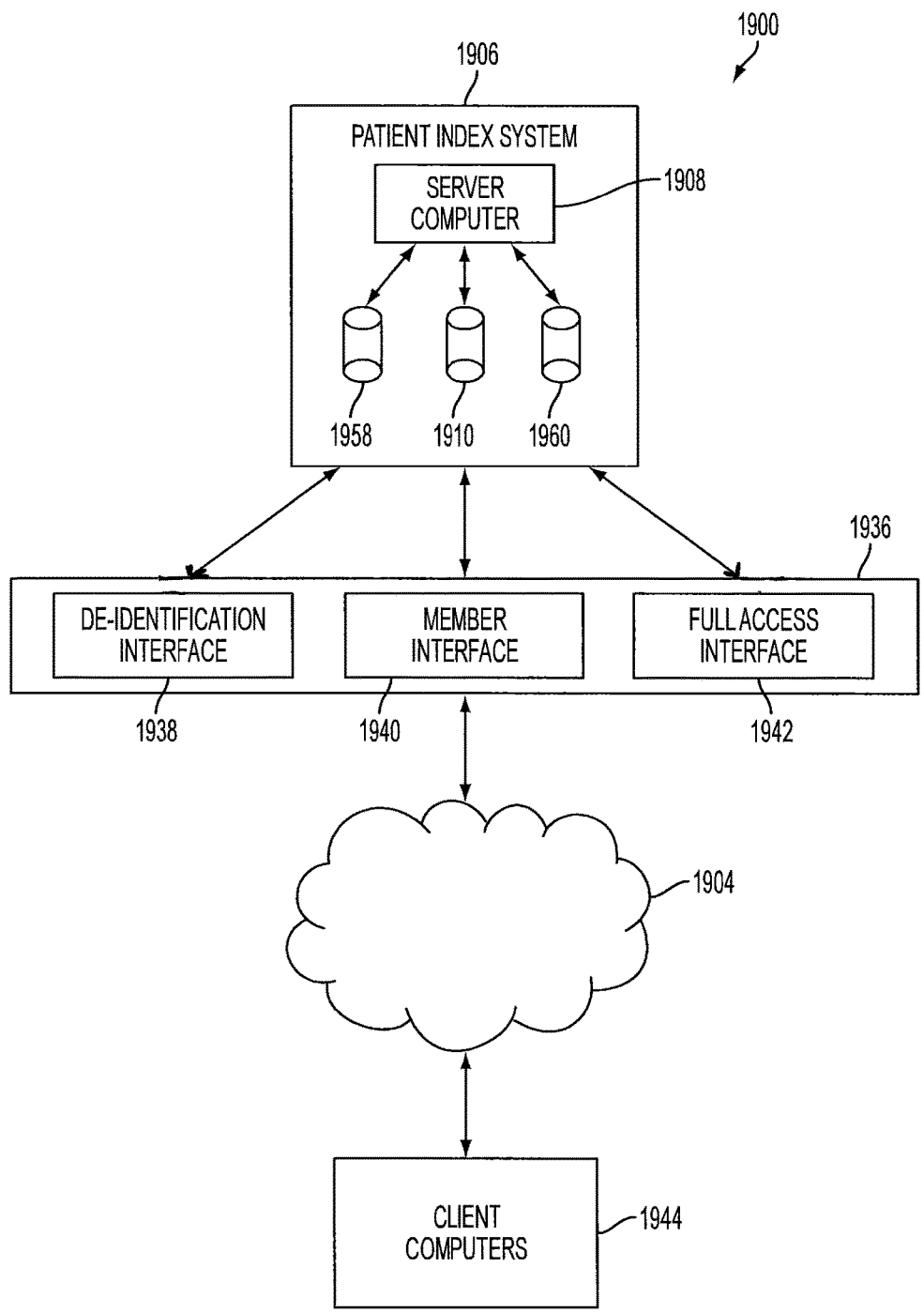
FIG. 19 illustrates a system for generating geographic analytics from patient records.

FIGS. 19-30 illustrate examples of a system and processes for generating geographic analytics using a patient index system. FIG. 19 illustrates a system 1900 for generating geographic analytics from patient records that include PE records. The system 1900 includes a patient index system 1906, an analytics interface 1936, a network 1904, and one or more client computers 1944. The analytics interface 1936 includes a de-identification interface 1938, a member interface 1940, and a full-access interface 1942. The patient index system 1906 includes at least one server computer 1908, a data warehouse 1910, a maps repository 1958, and an environmental-data repository 1960.

In a typical embodiment, the system 1900 provides functionality similar to the system 500 of FIG. 5. Thus, the at least one server computer 1908, the analytics interface 1936 (and subcomponents), the network 1904, the one or more client computers 1944, and the data warehouse 1910 can operate similarly to the at least one server computer 1508, the analytics interface 536 (and subcomponents), the network 504, the one or more client computers 544, and the data warehouse 510, respectively. In addition, in a typical embodiment, the system 1900 is operable to provide functionality similar to the system 1600 of FIG. 16. As described in greater detail below, via the maps repository 1958 and the environmental-data repository 1960, the system 1900 is operably to provide geographic analytics.

In particular, the data warehouse 1910 maintains patient records (and PE records) that include, for example, ZIP codes, cities, counties, states, countries, or the like, for patients. Thus, the data warehouse 1910 includes base data that includes at least some geographic information. The map repository 1958 includes maps suited to cover geographic units for which the data warehouse 1610 stores data. For example, the map repository may include maps to cover a region for which the patient index system receives PE records.

The environmental-data repository 1960 includes a set of environmental data for each of a plurality of environmental factors. The environmental-data repository 1960 is typically indexed by at least one geographic unit such as, for example, ZIP code. The environmental-data repository may include, for example, census data, United States Department of Agriculture (USDA) data, and other similar data. FIGS. 20-30 illustrate examples of operation for the system 1900.

Figure 20:
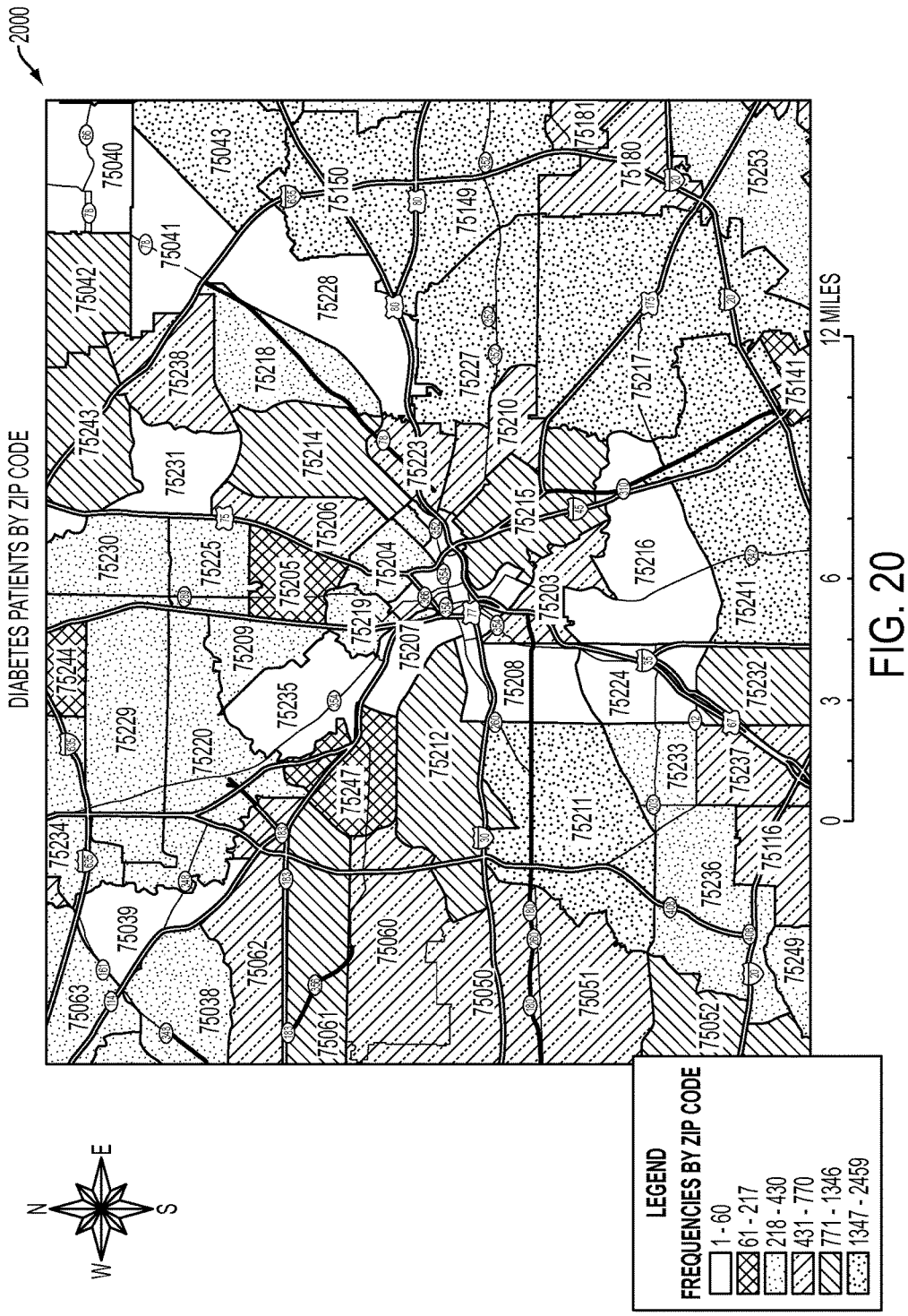
FIGS. 20-31 are exemplary maps that can be generated by a patient index system.

FIG. 20 is an exemplary map 2000 that, in various embodiments, can be generated by a patient index system with geographic-analytics functionality. Specifically, the map 2000 illustrates a frequency of diabetic patients, by ZIP code, throughout a region. In various embodiments, a number of diabetic patients is obtained by causing the at least one server computer 1908 to query the data warehouse 1910 for a number of PIDs that have a diagnosis code for diabetes. By aggregating the diabetic patients by zip code, cross-referencing with a map from the maps repository 1958, and annotating the map, the map 2000 can be displayed, for example, on one of the one or more client computers 1944.

Figure 21:
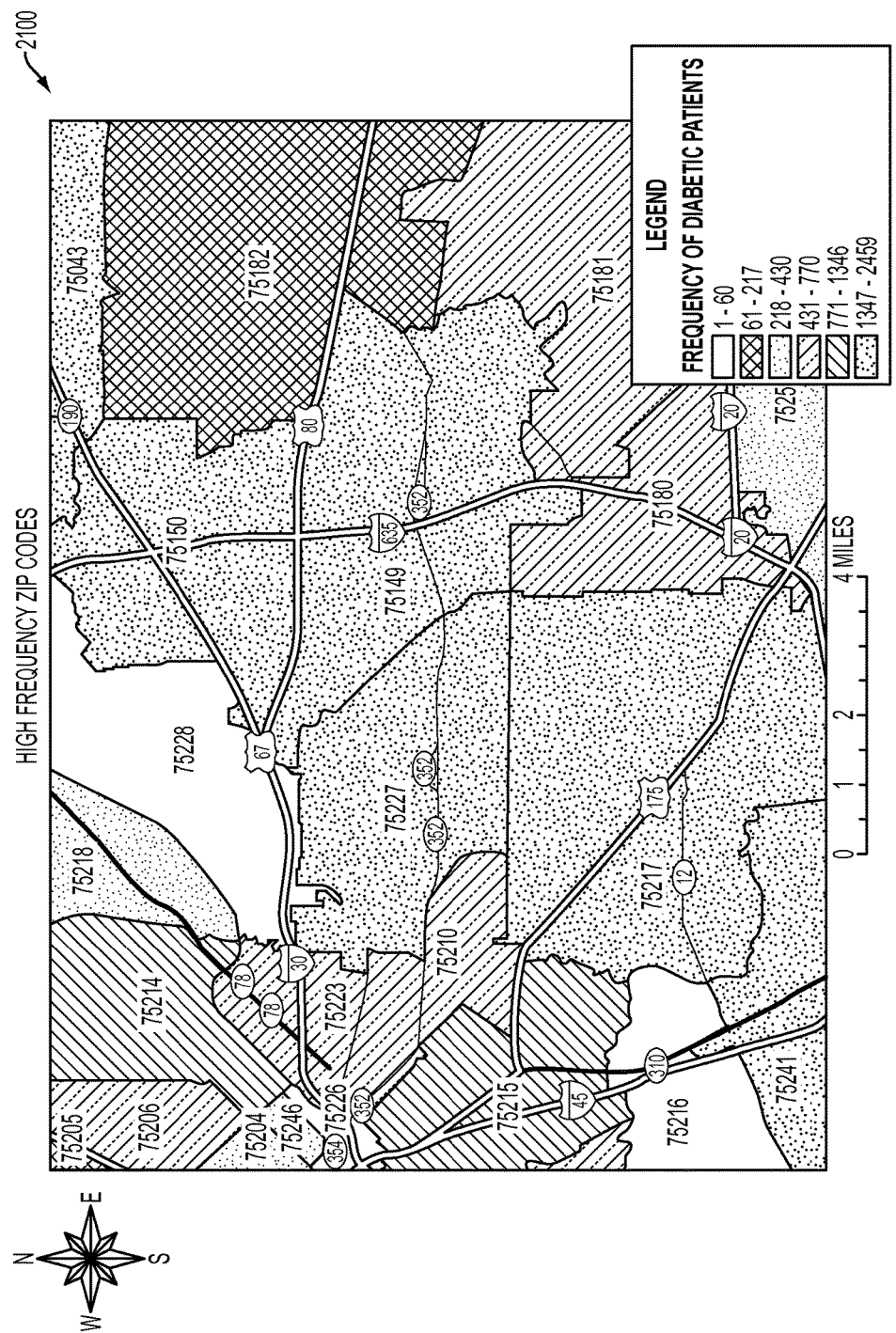

FIG. 21 is an exemplary map 2100 that, in various embodiments, can be generated by a patient index system with geographic-analytics functionality. The map 2100 is a zoomed-in version of the map 2000 of FIG. 20. In various embodiments, an analytics application on the at least one server computer 1908 permits a user on the one or more client computers 1944 to zoom-in via a command such as, for example, a mouse click. The map 2100 focuses on ZIP-code regions with a highest prevalence of diabetic patients.

Figure 22:
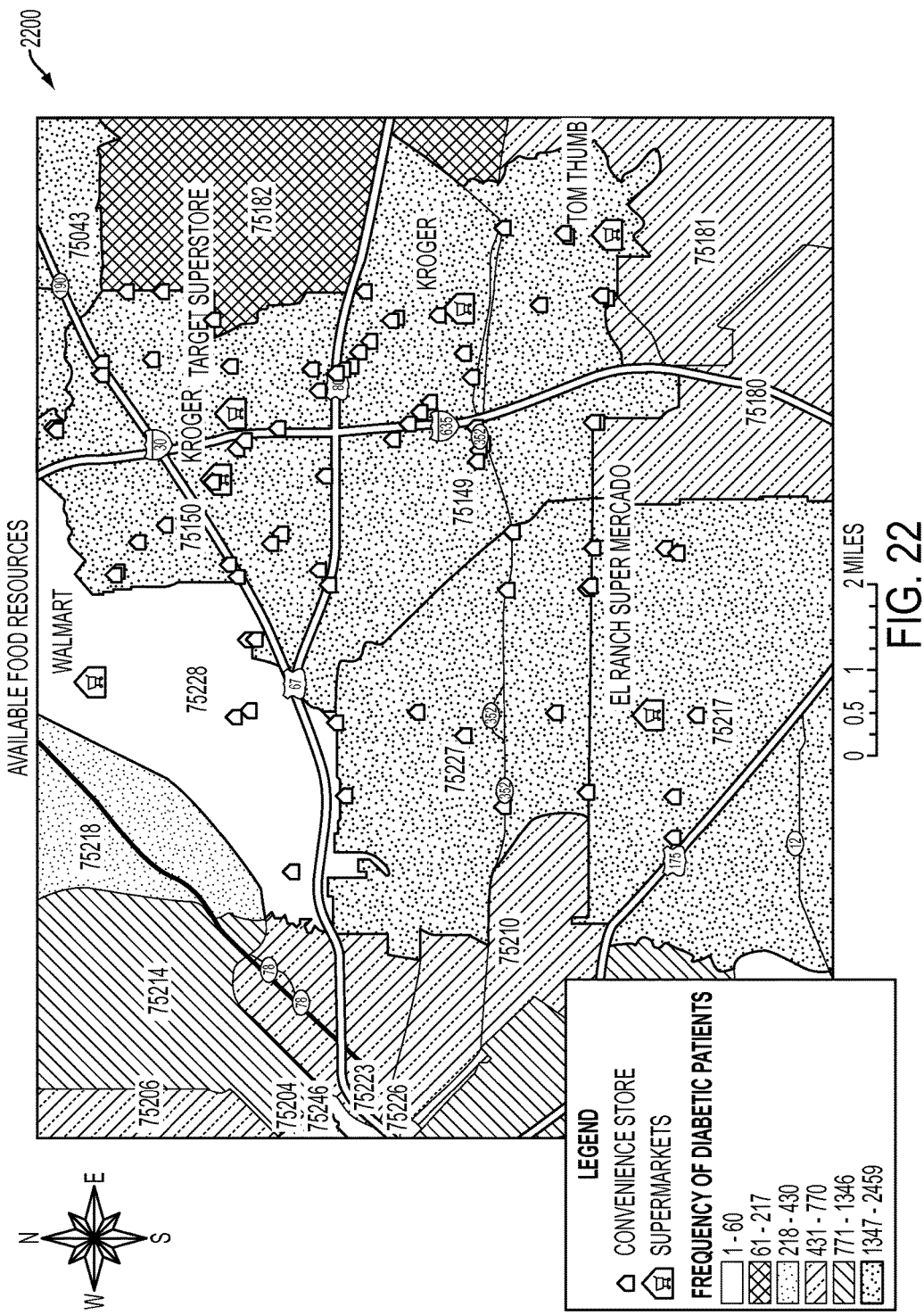

FIG. 22 is an exemplary map 2200 that, in various embodiments, can be generated by a patient index system with geographic-analytics functionality. The map 2200 adds a new layer for an environmental factor of available food resources. In various embodiments, the new layer may be added via an interface provided by an analytics application operating on the at least one server computer 1908 of FIG. 19. The map 2200 is a composite map that illustrates a prevalence of diabetic patients and an environmental factor of available food resources. By way of example, the map 2200 indicates that ZIP codes having a high prevalence of diabetic patients also have a relative paucity of supermarkets and a relatively high prevalence of convenience stores.

Figure 23:
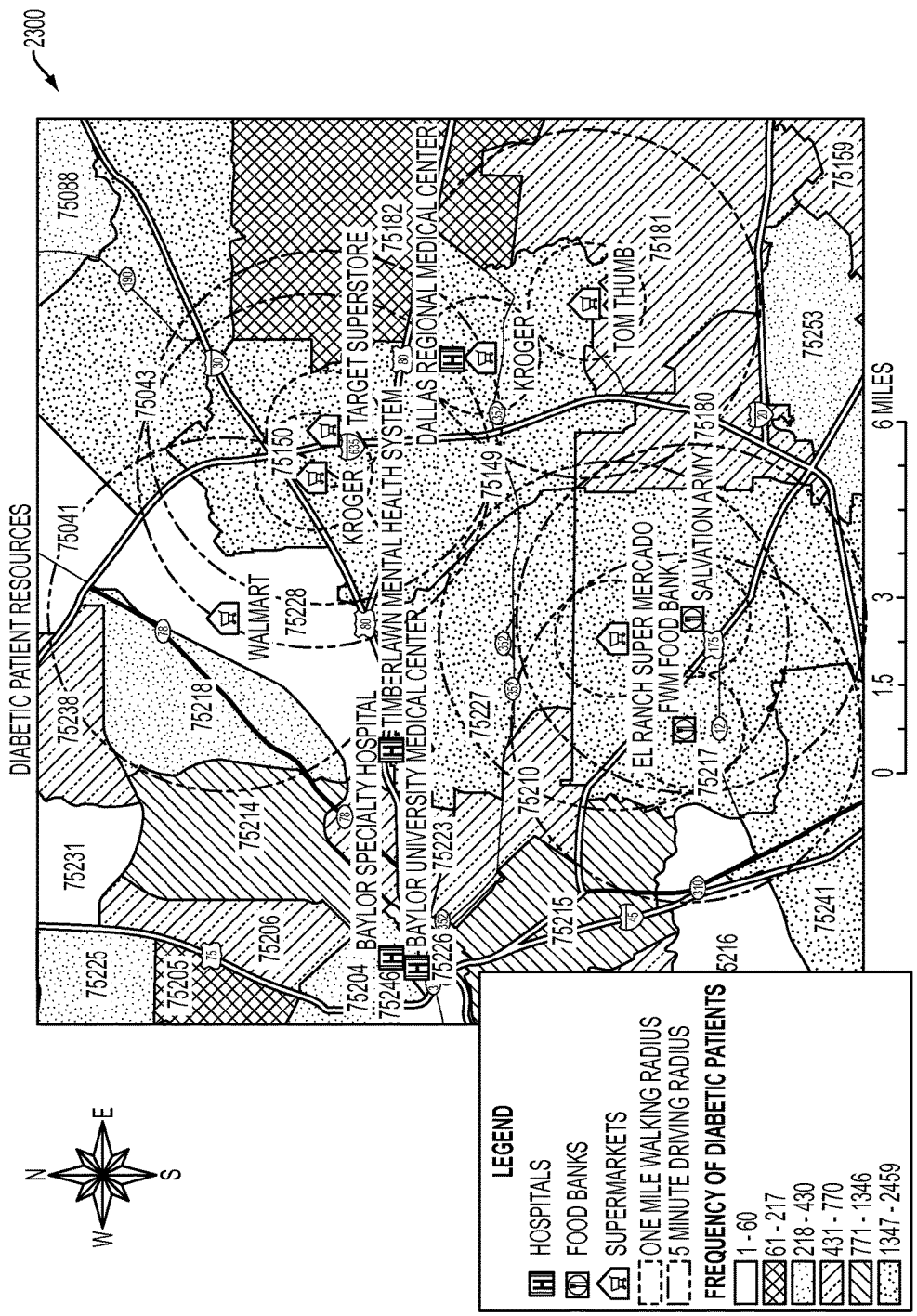

FIG. 23 is an exemplary map 2300 that, in various embodiments, can be generated by a patient index system with geographic-analytics functionality. The map 2300 is a composite map that adds new layers for environmental factors of hospital availability, food-bank availability, and supermarket availability. In addition, the map 2300 adds new layers to illustrate a walking radius and a driving radius for each supermarket and food bank. The map 2300 indicates that ZIP codes having a high prevalence of diabetic patients also have very limited access to supermarkets and food banks within a walking or driving radius.

Figure 24:
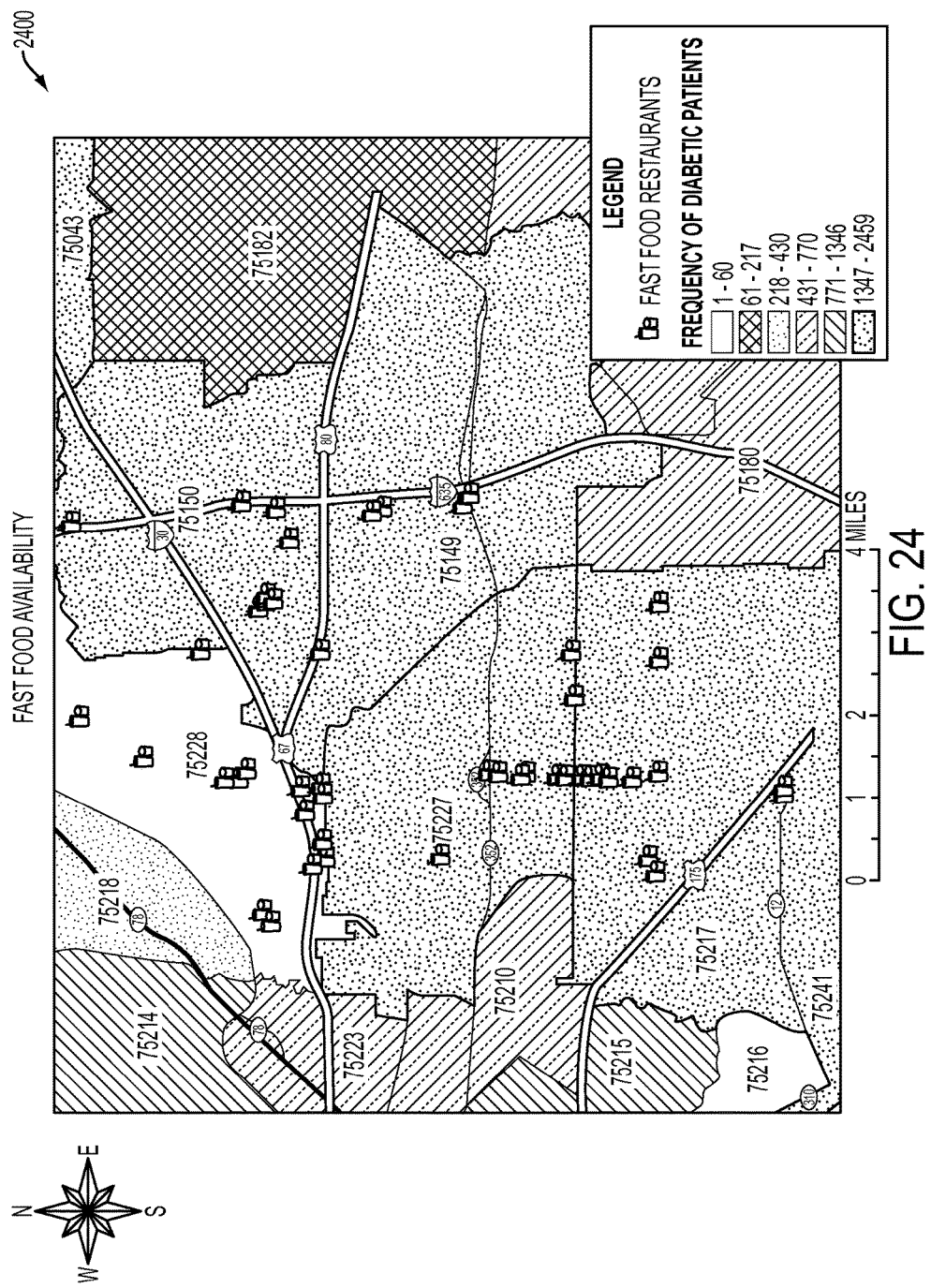

FIG. 24 is an exemplary map 2400 that, in various embodiments, can be generated by a patient index system with geographic-analytics functionality. The map 2400 is a composite map that adds a new layer for an environmental factor of fast-food availability. For example, the map 2400 indicates that ZIP codes having a high prevalence of diabetic patients also have very easy access to fast-food restaurants.

Figure 25:
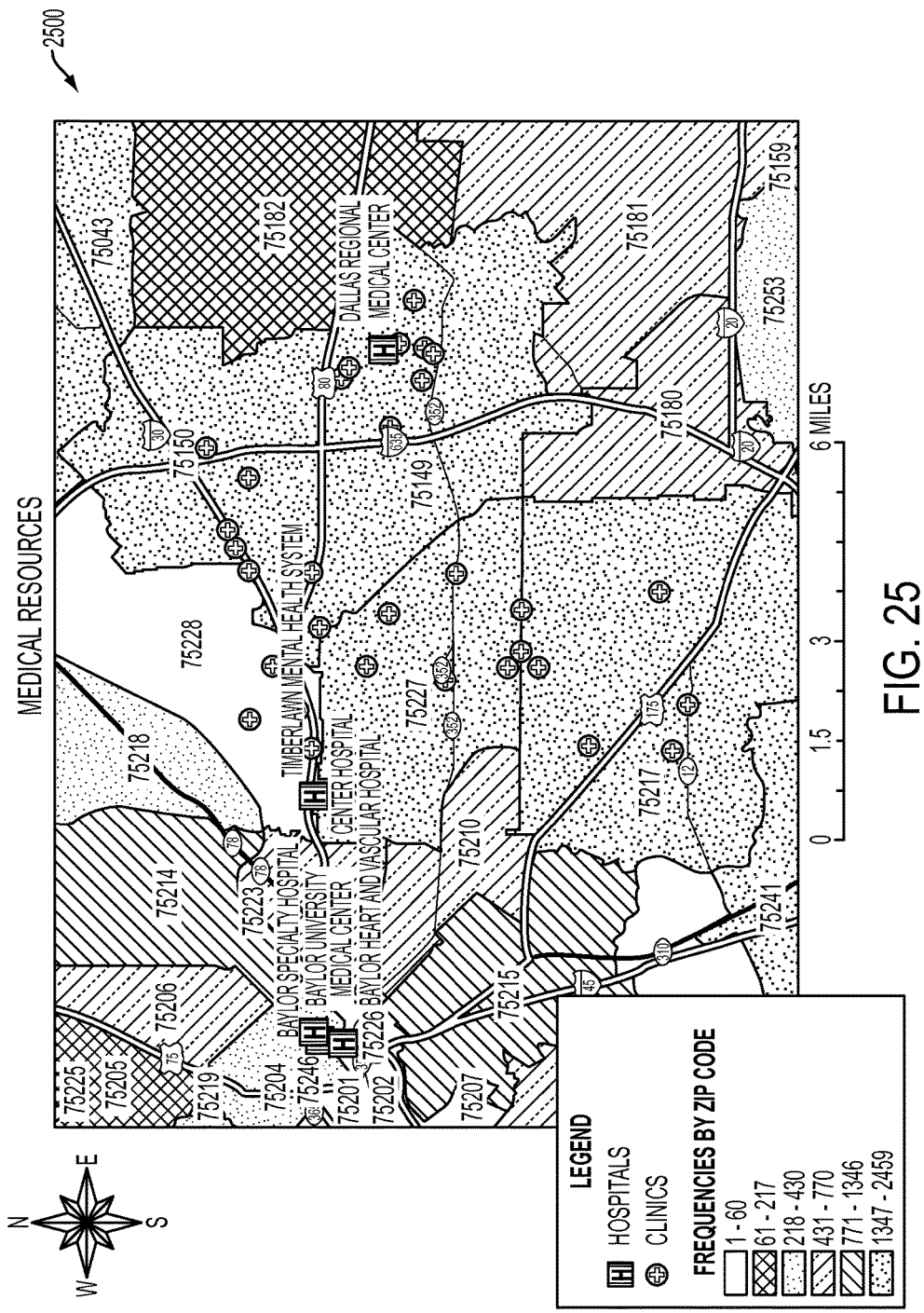

FIG. 25 is an exemplary map 2500 that, in various embodiments, can be generated by a patient index system with geographic-analytics functionality. The map 2500 is a composite map that adds new layers for hospital and clinic availability. For example, the map 2500 indicates that ZIP codes having a high prevalence of diabetic patients have hospitals and clinics in clusters as opposed to an even distribution throughout the region.

Figure 26:
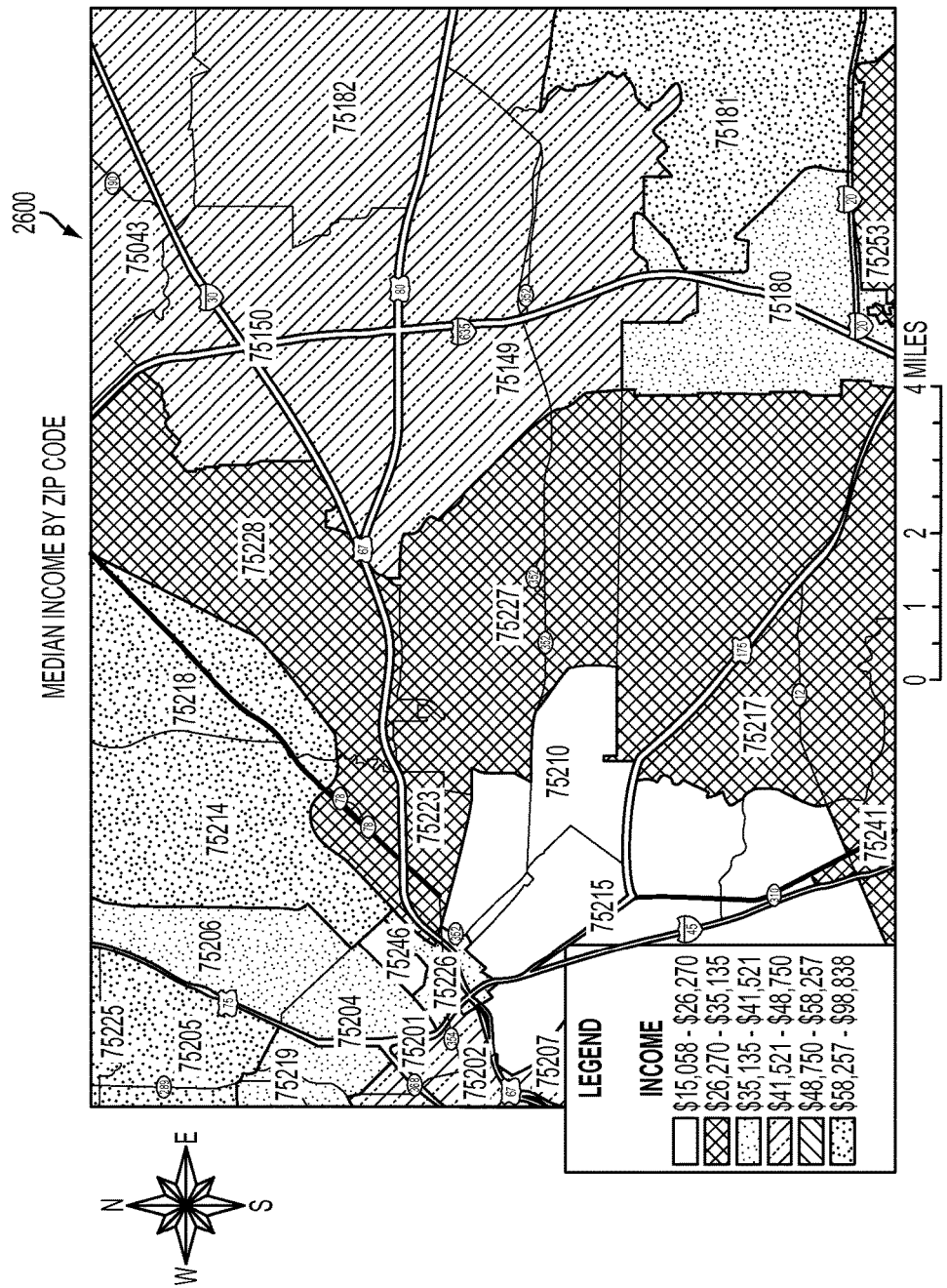

FIG. 26 is an exemplary map 2600 that, in various embodiments, can be generated by a patient index system with geographic-analytics functionality. The map 2600 adds a new layer for median income. For example, the map 2600 indicates, in combination with the maps described above, that ZIP codes having a high prevalence of diabetic patients have relatively low income.

Figure 27:
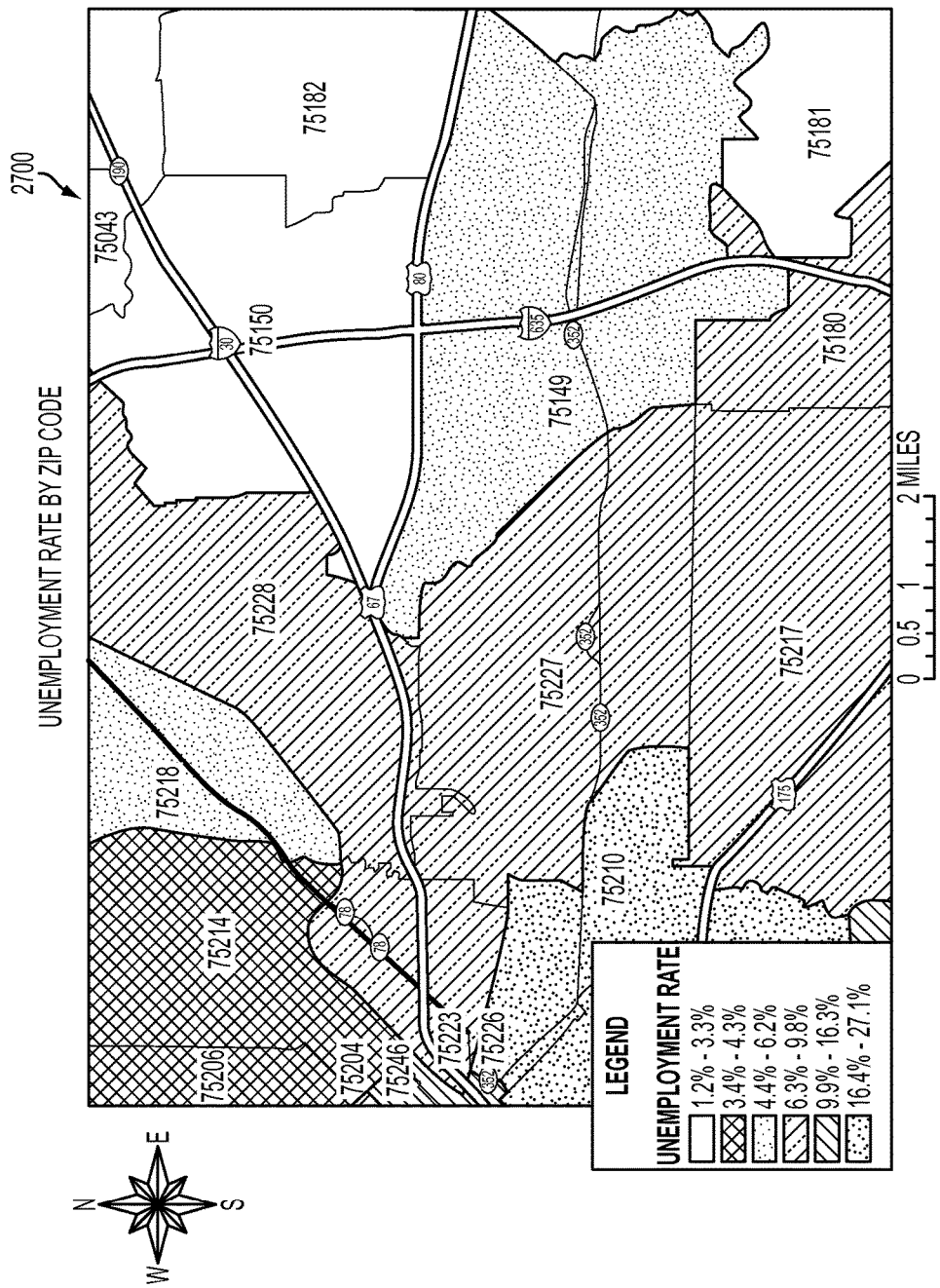

FIG. 27 is an exemplary map 2700 that, in various embodiments, can be generated by a patient index system with geographic-analytics functionality. The map 2700 adds a new layer for unemployment rate. For example, the map 2700 indicates, in combination with the maps described above, that ZIP codes having a high prevalence of diabetic patients have a high unemployment rate.

Figure 28:
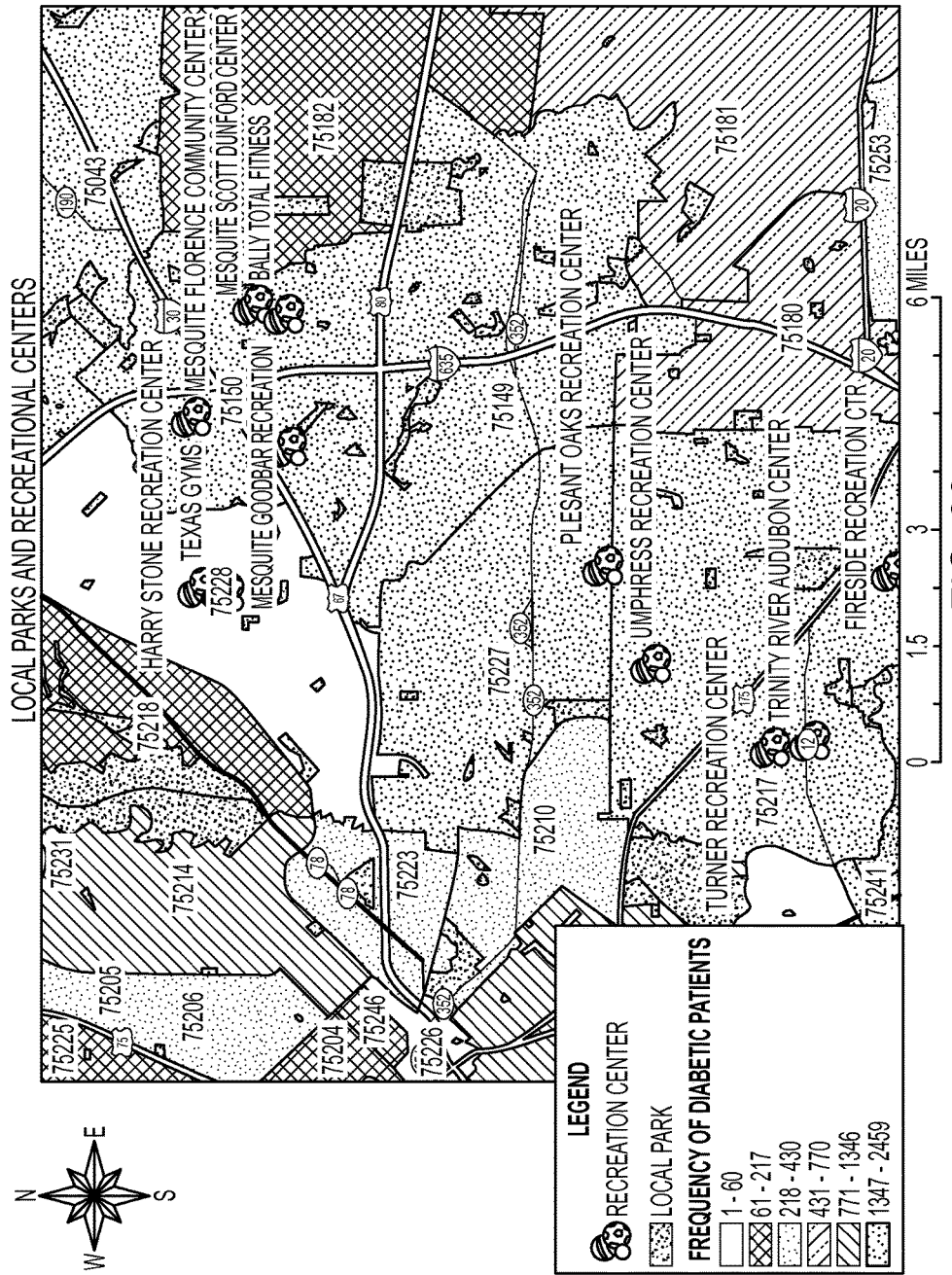

FIG. 28 is an exemplary map 2800 that, in various embodiments, can be generated by a patient index system with geographic-analytics functionality. The map 2800 is a composite map that adds new layers for an availability of recreation centers and local parks. For example, the map 2800 indicates that ZIP codes having a high prevalence of diabetic patients have relatively few parks and recreation centers.

Figure 29:
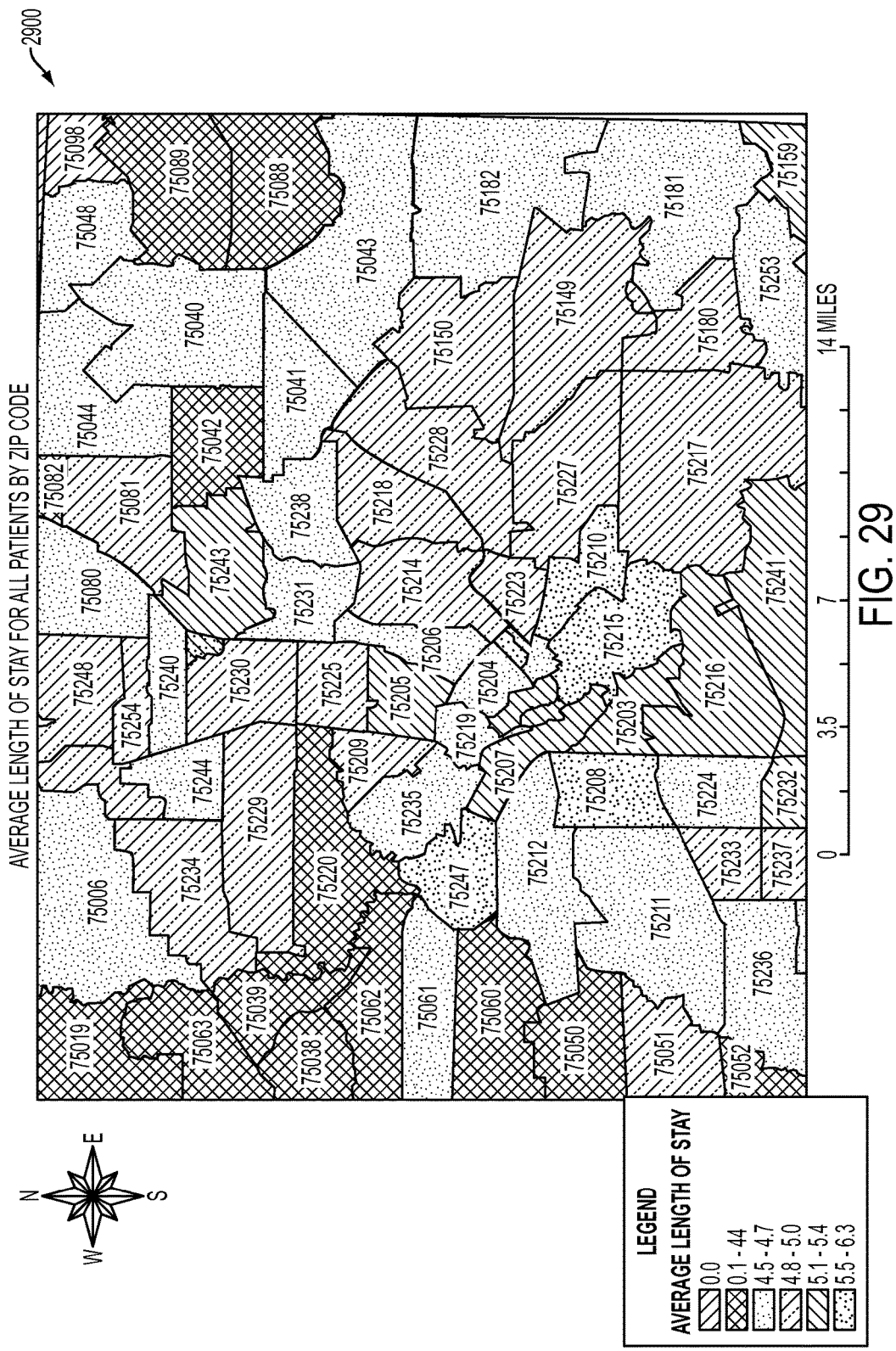

FIG. 29 is an exemplary map 2900 that, in various embodiments, can be generated by a patient index system with geographic-analytics functionality. The map 2900 adds a new layer for the average of length of stay by diabetic patients in a hospital.

Figure 30:
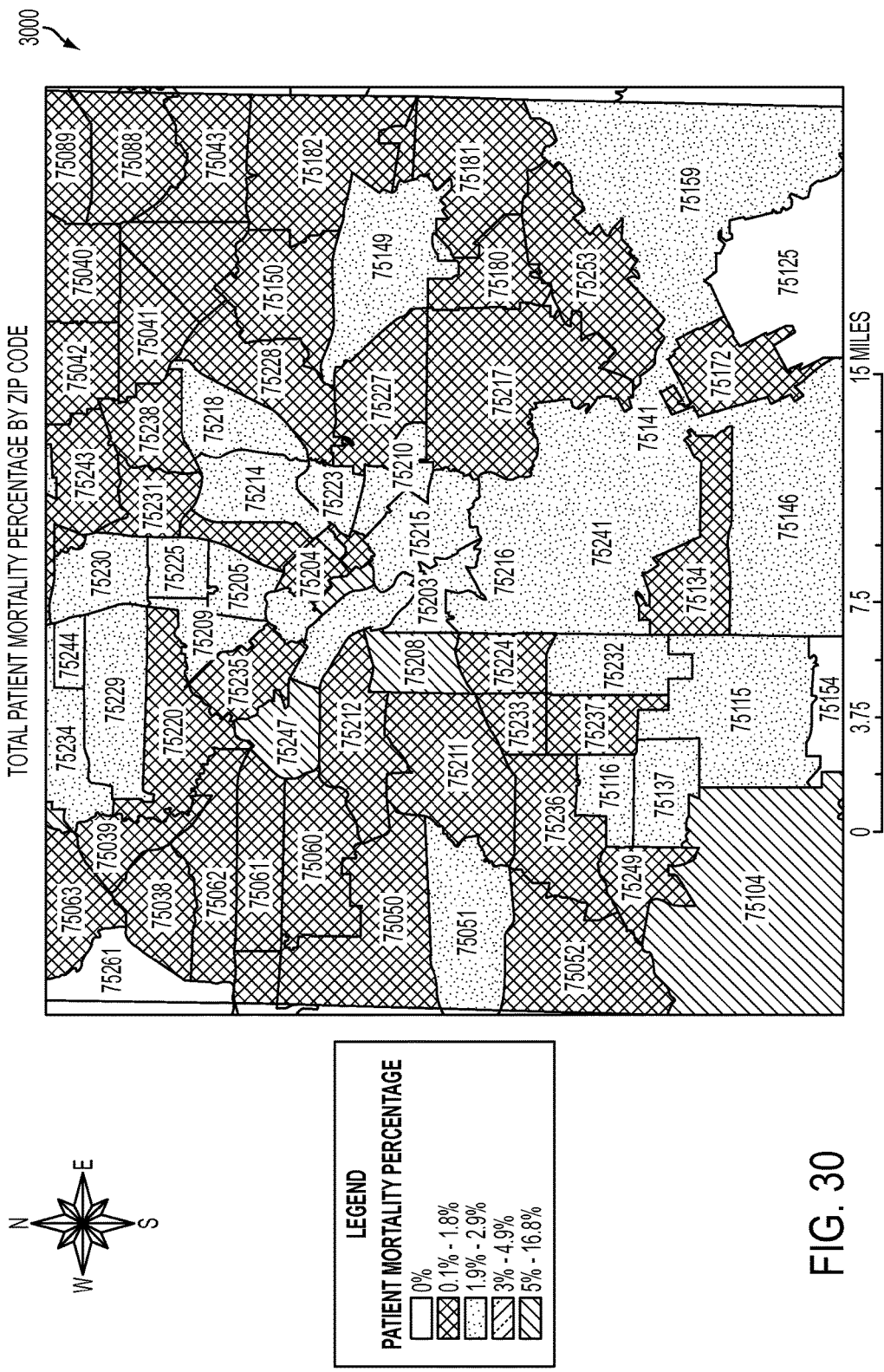

FIG. 30 is an exemplary map 3000 that, in various embodiments, can be generated by a patient index system with geographic-analytics functionality. The map 3000 adds a new layer for patient-mortality rates when diabetic patients were admitted to the hospital. In various embodiments, deaths can be detected via a discharge-disposition field in PE records.

Figure 31:
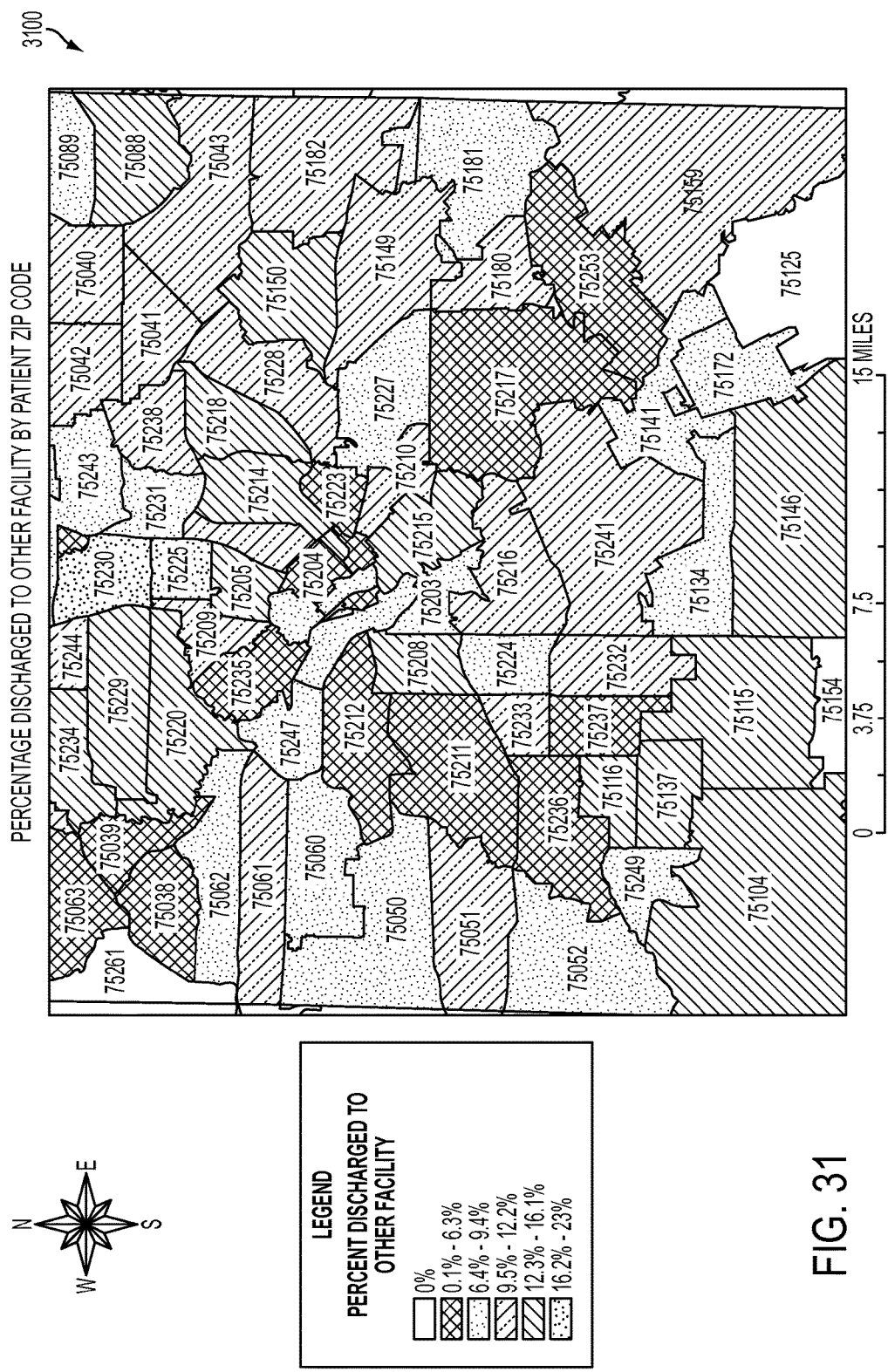

FIG. 31 is an exemplary map 3100 that, in various embodiments, can be generated by a patient index system with geographic-analytics functionality. The map 3100 adds a new layer for a percentage of diabetic patients that were discharged to another facility (e.g., a nursing home) rather than being sent home. In various embodiments, transfers to another facility can be detected via a discharge-disposition field in PE records.

One of ordinary skill in the art will appreciate that, in various embodiments, many types of environmental factors are available. Examples appear in Tables 12-13 below.

TABLE 12

| CATEGORY | EXEMPLARY ENVIRONMENTAL FACTORS |
|---|---|
| OCCUPANCY STATUS | Total Housing Units |
|  | Occupied Housing Units |
|  | Vacant Housing Units |
| VACANCY STATUS | Vacant Housing Units |
|  | For Rent and Not Rented |
|  | Rented, Not Occupied |

TABLE 13

| CATEGORY | EXEMPLARY ENVIRONMENTAL FACTORS |
|---|---|
| TENURE | Owner-Occupied Housing Units |
|  | Renter-Occupied Housing Units |
|  | Owned with a Mortgage or Loan |
|  | Owned Free and Clear |
| TENURE BY RACE OR ETHNICITY | Not Hispanic or Latino Householder |
|  | White-alone Householder |
|  | African-American Alone Householder |
|  | American Indian and Alaska Native Alone Householder |
|  | Asian Alone householder |
|  | Native Hawaiian and Other Pacific Islander Alone Householder |
|  | Some Other Race Alone Householder |
|  | Two or More Races householder |
|  | Hispanic or Latino Householder |

Although various embodiments of the method and apparatus of the present invention have been illustrated in the accompanying Drawings and described in the foregoing Detailed Description, it will be understood that the invention is not limited to the embodiments disclosed, but is capable of numerous rearrangements, modifications and substitutions without departing from the spirit of the invention as set forth herein.

What is claimed is:

1. A method comprising:
separately maintaining, by a server computer, a base-data repository, a map repository, and an environmental-data repository;
wherein access to particular fields of particular records of the base-data repository is disabled subject to a grouping requirement, the particular fields of the particular records storing personal information;
wherein the grouping requirement overrides the disablement of access to the particular fields of the particular records and allows access to the particular fields of the particular records when the particular fields of the particular records are accessed aggregately as part of a group of records that include the particular fields, such that the particular records of the base-data repository are not viewable individually, and such that the group includes at least a set number of records;
wherein the base-data repository comprises a set of records which includes analytic metrics in relation to geographic information;
wherein the environmental-data repository comprises data about particular geographic units;
receiving, by the server computer, a selection of base data of the base-data repository;
subject to the grouping requirement, aggregating the selection of base data by geographic unit based on at least one analytic metric;
accessing, by the server computer, from the map repository, a map of a geographic region covered by the selection of base data;
receiving, by the server computer, a selection of at least one environmental factor;
aggregating, by the server computer, from the environmental-data repository, environmental data for the at least one environmental factor by the geographic unit; and
generating, by the server computer, a multi-layered geographic visualization of the selection of base data, the generating comprising creating a composite map that is annotated with a geographic variance of the at least one environmental factor together with a geographic variance of the at least one analytic metric.

2. The method of claim 1, the method comprising displaying the multi-layered geographic visualization to a requestor.

3. The method of claim 1, wherein the selection of base data is received via a de-identification interface.

4. The method of claim 1, wherein the at least one analytic metric relates to a prevalence of a condition.

5. The method of claim 4, wherein:
the selection of base data comprises selection of patient-encounter records; and
the condition is identified via at least one diagnosis code within the patient-encounter records.

6. The method of claim 1, wherein the at least one environmental factor relates to distance from a resource.

7. The method of claim 1, wherein the at least one environmental factor relates to occupancy status.

8. The method of claim 1, wherein the at least one environmental factor relates to tenure.

9. The method of claim 1, wherein the geographic unit is identified by a ZIP code.

10. A computer-program product comprising a non-transitory computer-usable medium having computer-readable program code embodied therein, the computer-readable program code adapted to be executed to implement a method comprising:

separately maintaining a base-data repository, a map repository, and an environmental-data repository;

wherein access to particular fields of particular records of the base-data repository is disabled subject to a grouping requirement, the particular fields of the particular records storing personal information;

wherein the grouping requirement overrides the disablement of access to the particular fields of the particular records and allows access to the particular fields of the particular records when the particular fields of the particular records are accessed aggregately as part of a group of records that include the particular fields, such that the particular records of the base-data repository are not viewable individually, and such that the group includes at least a set number of records;

wherein the base-data repository comprises a set of records which includes analytic metrics in relation to geographic information;

wherein the environmental-data repository comprises data about particular geographic units;

receiving, by, a selection of base data of the base-data repository;

subject to the grouping requirement, aggregating the selection of base data by geographic unit based on at least one analytic metric;

accessing, from the map repository, a map of a geographic region covered by the selection of base data;

receiving a selection of at least one environmental factor;

aggregating, from the environmental-data repository, environmental data for the at least one environmental factor by the geographic unit; and generating a multi-layered geographic visualization of the selection of base data, the generating comprising creating a composite map that is annotated with a geographic variance of the at least one environmental factor together with a geographic variance of the at least one analytic metric.

11. The computer-program product of claim 10, the method comprising displaying the multi-layered geographic visualization to a requestor.

12. The computer-program product of claim 10, wherein the selection of base data is received via a de-identification interface.

13. The computer-program product of claim 10, wherein the at least one analytic metric relates to a prevalence of a condition.

14. The computer-program product of claim 13, wherein:
the selection of base data comprises selection of patient-encounter records; and
the condition is identified via at least one diagnosis code within the patient-encounter records.

15. The computer-program product of claim 10, wherein the at least one environmental factor relates to distance from a resource.

16. The computer-program product of claim 10, wherein the at least one environmental factor relates to occupancy status.

17. The computer-program product of claim 10, wherein the at least one environmental factor relates to tenure.

18. The computer-program product of claim 10, wherein the geographic unit is identified by a ZIP code.

* * * * *